(12) United States Patent
Sakurai et al.

(10) Patent No.: US 9,862,929 B2
(45) Date of Patent: Jan. 9, 2018

(54) METHOD OF INDUCING DIFFERENTIATION FROM PLURIPOTENT STEM CELLS TO SKELETAL MUSCLE CELLS

(75) Inventors: Hidetoshi Sakurai, Kyoto (JP); Akihito Tanaka, Kyoto (JP); Knut Woltjen, Kyoto (JP); Makoto Ikeya, Kyoto (JP)

(73) Assignee: Kyoto University, Kyoto (JP)

( * ) Notice: Subject to any disclaimer, the term of this patent is extended or adjusted under 35 U.S.C. 154(b) by 64 days.

(21) Appl. No.: 14/357,982

(22) PCT Filed: Aug. 17, 2012

(86) PCT No.: PCT/JP2012/071373
§ 371 (c)(1),
(2), (4) Date: Jul. 24, 2014

(87) PCT Pub. No.: WO2013/073246
PCT Pub. Date: May 23, 2013

(65) Prior Publication Data
US 2014/0370537 A1    Dec. 18, 2014

Related U.S. Application Data

(60) Provisional application No. 61/561,586, filed on Nov. 18, 2011.

(51) Int. Cl.
*C12N 5/00* (2006.01)
*C12N 5/077* (2010.01)
*C12N 15/85* (2006.01)
*G01N 33/50* (2006.01)

(52) U.S. Cl.
CPC ........... *C12N 5/0658* (2013.01); *C12N 15/85* (2013.01); *G01N 33/5061* (2013.01); *C12N 2506/45* (2013.01); *C12N 2510/00* (2013.01); *C12N 2800/22* (2013.01)

(58) Field of Classification Search
CPC ............................. C12N 5/0658; C12N 15/85
See application file for complete search history.

(56) References Cited

U.S. PATENT DOCUMENTS 6,432,711 B1 *   8/2002   Dinsmore ............ C07K 14/475
                                                435/325
2001/0016952 A1 * 8/2001   Campbell .......... A01K 67/0276
                                                800/18

FOREIGN PATENT DOCUMENTS

WO    WO 2010/008100 A1    1/2010

OTHER PUBLICATIONS

Schuldiner et al. PNAS 97(21):11307-11312, 2000.*
Gunaseeli et al. Curr Med Chem 17(8):759-766, 2010.*
Buchberger et al., *Development*, 134(6): 1171-1180 (2007).
Dekel et al., *New Biol.*, 4(3): 217-224 (1992).
Gianakopoulos et al., *J. Biol. Chem.*, 286(4): 2517-2525 (2011).
Mahmood et al., *J. Bone Miner. Res.*, 25(6): 1216-1233 (2010).
Miyoshi et al., *Brain*, 109(1): 31-54 (1986) [summary only].
Mizuno et al., *FASEB J.*, 24(7): 2245-2253 (2010).
Mizuno et al., *Plast. Reconstr. Surg.*, 109(1): 199-209 (2002).
Ozasa et al., *Biochem. Biophys. Res. Commun.*, 357(4): 957-963 (2007).
Sakaguchi et al., *Abstracts of the Annual Meeting of the Molecular Biology Society of Japan*, 32(2): 193, abstract 2P-0612 (2009).
Sakurai et al., *Stem Cell Res.*, 3(2-3): 157-169 (2009).
Tanaka et al., "Establishment of efficient skeletal muscle induction from human induced pluripotent stem cell using transcription factor," *Regen. Med.*, 11 (Suppl): 211 (2012).
Tapscott et al., *Science*, 242: 405-411 (1988).
Tashiro et al., *Stem Cells*, 27(8): 1802-1811 (2009).
Warren et al., *Cell Stem Cell*, 7(5): 618-630 (2010).
Japan Patent Office, International Search Report in International Patent Application No. PCT/2012/071373 (dated Nov. 27, 2012).
Tanaka et al., "Efficient and Reproducible Myogenic Differentiation from Human iPS Cells: Prospects for Modeling Miyoshi Myopathy In Vitro," *PLOS One*, 8(4): e61540 (2013).

* cited by examiner

*Primary Examiner* — Marcia S Noble
(74) *Attorney, Agent, or Firm* — Leydig, Voit & Mayer, Ltd.

(57) ABSTRACT

The present invention provides a method of producing a skeletal muscle cell from a pluripotent stem cell, which includes a step of expressing one or more exogenous factors selected from MyoD, Myf5 and nucleic acids encoding them on a pluripotent stem cell.

17 Claims, 15 Drawing Sheets
(13 of 15 Drawing Sheet(s) Filed in Color)

SEQUENCE LISTING

<160> NUMBER OF SEQ ID NOS: 42

<210> SEQ ID NO 1
<211> LENGTH: 1823
<212> TYPE: DNA
<213> ORGANISM: Homo sapiens
<220> FEATURE:
<221> NAME/KEY: CDS
<222> LOCATION: (221)..(1183)

<400> SEQUENCE: 1

```
gagaagctag gggtgaggaa gccctggggc gctgccgccg ctttccttaa ccacaaatca      60
ggccggacag gagagggagg ggtgggggac agtgggtggg cattcagact gccagcactt     120
tgctatctac agccggggct cccgagcggc agaaagttcc ggccactctc tgccgcttgg     180
gttgggcgaa gccaggaccg tgccgcgcca ccgccaggat atg gag cta ctg tcg      235
                                             Met Glu Leu Leu Ser
                                              1               5 cca ccg ctc cgc gac gta gac ctg acg gcc ccc gac ggc tct ctc tgc      283
Pro Pro Leu Arg Asp Val Asp Leu Thr Ala Pro Asp Gly Ser Leu Cys
             10                  15                  20 tcc ttt gcc aca acg gac gac ttc tat gac gac ccg tgt ttc gac tcc      331
Ser Phe Ala Thr Thr Asp Asp Phe Tyr Asp Asp Pro Cys Phe Asp Ser
         25                  30                  35 ccg gac ctg cgc ttc ttc gaa gac ctg gac ccg cgc ctg atg cac gtg      379
Pro Asp Leu Arg Phe Phe Glu Asp Leu Asp Pro Arg Leu Met His Val
     40                  45                  50 ggc gcg ctc ctg aaa ccc gaa gag cac tcg cac ttc ccc gcg gcg gtg      427
Gly Ala Leu Leu Lys Pro Glu Glu His Ser His Phe Pro Ala Ala Val
 55                  60                  65 cac ccg gcc ccg ggc gca cgt gag gac gag cat gtg cgc gcg ccc agc      475
His Pro Ala Pro Gly Ala Arg Glu Asp Glu His Val Arg Ala Pro Ser
 70                  75                  80                  85 ggg cac cac cag gcg ggc cgc tgc cta ctg tgg gcc tgc aag gcg tgc      523
Gly His His Gln Ala Gly Arg Cys Leu Leu Trp Ala Cys Lys Ala Cys
                 90                  95                 100 aag cgc aag acc acc aac gcc gac cgc cgc aag gcc gcc acc atg cgc      571
Lys Arg Lys Thr Thr Asn Ala Asp Arg Arg Lys Ala Ala Thr Met Arg
            105                 110                 115 gag cgg cgc cgc ctg agc aaa gta aat gag gcc ttt gag aca ctc aag      619
Glu Arg Arg Arg Leu Ser Lys Val Asn Glu Ala Phe Glu Thr Leu Lys
        120                 125                 130 cgc tgc acg tcg agc aat cca aac cag cgg ttg ccc aag gtg gag atc      667
Arg Cys Thr Ser Ser Asn Pro Asn Gln Arg Leu Pro Lys Val Glu Ile
    135                 140                 145 ctg cgc aac gcc atc cgc tat atc gag ggc ctg cag gct ctg ctg cgc      715
Leu Arg Asn Ala Ile Arg Tyr Ile Glu Gly Leu Gln Ala Leu Leu Arg
150                 155                 160                 165 gac cag gac gcc gcg ccc cct ggc gcc gca gcc gcc ttc tat gcg ccg      763
Asp Gln Asp Ala Ala Pro Pro Gly Ala Ala Ala Ala Phe Tyr Ala Pro
                170                 175                 180 ggc ccg ctg ccc ccg ggc cgc ggc ggc gag cac tac agc ggc gac tcc      811
Gly Pro Leu Pro Pro Gly Arg Gly Gly Glu His Tyr Ser Gly Asp Ser
            185                 190                 195 gac gcg tcc agc ccg cgc tcc aac tgc tcc gac ggc atg atg gac tac      859
Asp Ala Ser Ser Pro Arg Ser Asn Cys Ser Asp Gly Met Met Asp Tyr
        200                 205                 210 agc ggc ccc ccg agc ggc gcc cgg cgg cgg aac tgc tac gaa ggc gcc      907
Ser Gly Pro Pro Ser Gly Ala Arg Arg Arg Asn Cys Tyr Glu Gly Ala
    215                 220                 225
```

| | | | | | | | | | | | | | | | | |
|---|---|---|---|---|---|---|---|---|---|---|---|---|---|---|---|---|
| tac | tac | aac | gag | gcg | ccc | agc | gaa | ccc | agg | ccc | ggg | aag | agt | gcg | gcg | 955 |
| Tyr | Tyr | Asn | Glu | Ala | Pro | Ser | Glu | Pro | Arg | Pro | Gly | Lys | Ser | Ala | Ala | |
| 230 | | | | | 235 | | | | | 240 | | | | | 245 | |
| gtg | tcg | agc | cta | gac | tgc | ctg | tcc | agc | atc | gtg | gag | cgc | atc | tcc | acc | 1003 |
| Val | Ser | Ser | Leu | Asp | Cys | Leu | Ser | Ser | Ile | Val | Glu | Arg | Ile | Ser | Thr | |
| | | | 250 | | | | | 255 | | | | | 260 | | | |
| gag | agc | cct | gcg | gcg | ccc | gcc | ctc | ctg | ctg | gcg | gac | gtg | cct | tct | gag | 1051 |
| Glu | Ser | Pro | Ala | Ala | Pro | Ala | Leu | Leu | Leu | Ala | Asp | Val | Pro | Ser | Glu | |
| | | | 265 | | | | | 270 | | | | | 275 | | | |
| tcg | cct | ccg | cgc | agg | caa | gag | gct | gcc | gcc | ccc | agc | gag | gga | gag | agc | 1099 |
| Ser | Pro | Pro | Arg | Arg | Gln | Glu | Ala | Ala | Ala | Pro | Ser | Glu | Gly | Glu | Ser | |
| | | 280 | | | | | 285 | | | | | 290 | | | | |
| agc | ggc | gac | ccc | acc | cag | tca | ccg | gac | gcc | gcc | ccg | cag | tgc | cct | gcg | 1147 |
| Ser | Gly | Asp | Pro | Thr | Gln | Ser | Pro | Asp | Ala | Ala | Pro | Gln | Cys | Pro | Ala | |
| | 295 | | | | | 300 | | | | | 305 | | | | | |
| ggt | gcg | aac | ccc | aac | ccg | ata | tac | cag | gtg | ctc | tga | ggggatggtg | | | | 1193 |
| Gly | Ala | Asn | Pro | Asn | Pro | Ile | Tyr | Gln | Val | Leu | | | | | | |
| 310 | | | | 315 | | | | | 320 | | | | | | | |

| | |
|---|---|
| gccgcccacc cgcccgaggg atggtgcccc tagggtccct cgcgcccaaa agattgaact | 1253 |
| taaatgcccc cctcccaaca gcgctttaaa agcgacctct cttgaggtag gagaggcggg | 1313 |
| agaactgaag tttccgcccc cgccccacag ggcaaggaca cagcgcggtt ttttccacgc | 1373 |
| agcacccttc tcggagaccc attgcgatgg ccgctccgtg ttcctcggtg ggccagagct | 1433 |
| gaaccttgag gggctaggtt cagctttctc gcgccctccc ccatgggggt gagaccctcg | 1493 |
| cagacctaag ccctgccccg ggatgcaccg gttatttggg gggcgtgag acccagtgca | 1553 |
| ctccggtccc aaatgtagca ggtgtaaccg taacccaccc ccaacccgtt tcccggttca | 1613 |
| ggaccacttt ttgtaatact tttgtaatct attcctgtaa ataagagttg ctttgccaga | 1673 |
| gcaggagccc ctggggctgt atttatctct gaggcatggt gtgtggtgct acagggaatt | 1733 |
| tgtacgttta taccgcaggc gggcgagccg cgggcgctcg ctcaggtgat caaaataaag | 1793 |
| gcgctaattt ataaaaaaaa aaaaaaaaaa | 1823 |

<210> SEQ ID NO 2
<211> LENGTH: 320
<212> TYPE: PRT
<213> ORGANISM: Homo sapiens

<400> SEQUENCE: 2

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Met His Val Gly Ala Leu Leu Lys Pro Glu Glu His Ser His
        50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu

```
                130                 135                 140
Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Gly Ala Ala Ala
                165                 170                 175

Ala Phe Tyr Ala Pro Gly Pro Leu Pro Pro Gly Arg Gly Glu His
                180                 185                 190

Tyr Ser Gly Asp Ser Asp Ala Ser Ser Pro Arg Ser Asn Cys Ser Asp
                195                 200                 205

Gly Met Met Asp Tyr Ser Gly Pro Pro Ser Gly Ala Arg Arg Arg Asn
                210                 215                 220

Cys Tyr Glu Gly Ala Tyr Tyr Asn Glu Ala Pro Ser Glu Pro Arg Pro
225                 230                 235                 240

Gly Lys Ser Ala Ala Val Ser Ser Leu Asp Cys Leu Ser Ser Ile Val
                245                 250                 255

Glu Arg Ile Ser Thr Glu Ser Pro Ala Ala Pro Ala Leu Leu Leu Ala
                260                 265                 270

Asp Val Pro Ser Glu Ser Pro Pro Arg Arg Gln Glu Ala Ala Ala Pro
                275                 280                 285

Ser Glu Gly Glu Ser Ser Gly Asp Pro Thr Gln Ser Pro Asp Ala Ala
                290                 295                 300

Pro Gln Cys Pro Ala Gly Ala Asn Pro Asn Pro Ile Tyr Gln Val Leu
305                 310                 315                 320

<210> SEQ ID NO 3
<211> LENGTH: 1520
<212> TYPE: DNA
<213> ORGANISM: Homo sapiens
<220> FEATURE:
<221> NAME/KEY: CDS
<222> LOCATION: (136)..(903)

<400> SEQUENCE: 3
tctgcccttg ttaattaccg gagcgacaga ctagggagct ccgcccggga tttgcccatc      60
ggcggaggcg ccaggctccc gtttctcccc atccctctcg ctgccgtcca ggtgcaccgc     120
ctgcctctca gcagg atg gac gtg atg gat ggc tgc cag ttc tca cct tct     171
                Met Asp Val Met Asp Gly Cys Gln Phe Ser Pro Ser
                 1               5                  10 gag tac ttc tac gac ggc tcc tgc ata ccg tcc ccc gag ggt gaa ttt      219
Glu Tyr Phe Tyr Asp Gly Ser Cys Ile Pro Ser Pro Glu Gly Glu Phe
            15                  20                  25 ggg gac gag ttt gtg ccg cga gtg gct gcc ttc gga gcg cac aaa gca      267
Gly Asp Glu Phe Val Pro Arg Val Ala Ala Phe Gly Ala His Lys Ala
 30                  35                  40 gag ctg cag ggc tca gat gag gac gag cac gtg cga gcg cct acc ggc      315
Glu Leu Gln Gly Ser Asp Glu Asp Glu His Val Arg Ala Pro Thr Gly
45                  50                  55                  60 cac cac cag gct ggt cac tgc ctc atg tgg gcc tgc aaa gcc tgc aag      363
His His Gln Ala Gly His Cys Leu Met Trp Ala Cys Lys Ala Cys Lys
                65                  70                  75 agg aag tcc acc acc atg gat cgg cgg aag gca gcc act atg cgc gag      411
Arg Lys Ser Thr Thr Met Asp Arg Arg Lys Ala Ala Thr Met Arg Glu
            80                  85                  90 cgg agg cgc ctg aag aag gtc aac cag gct ttc gaa acc ctc aag agg      459
Arg Arg Arg Leu Lys Lys Val Asn Gln Ala Phe Glu Thr Leu Lys Arg
        95                  100                 105 tgt acc acg acc aac ccc aac cag agg ctg ccc aag gtg gag atc ctc      507
```

| | | | | | | | | | | | | | | |
|---|---|---|---|---|---|---|---|---|---|---|---|---|---|---|
| Cys | Thr | Thr | Asn | Pro | Asn | Gln | Arg | Leu | Pro | Lys | Val | Glu | Ile | Leu |
| | 110 | | | | 115 | | | | 120 | | | | | |

| agg | aat | gcc | atc | cgc | tac | atc | gag | agc | ctg | cag | gag | ttg | ctg | aga | gag | 555 |
|---|---|---|---|---|---|---|---|---|---|---|---|---|---|---|---|---|
| Arg | Asn | Ala | Ile | Arg | Tyr | Ile | Glu | Ser | Leu | Gln | Glu | Leu | Leu | Arg | Glu | |
| 125 | | | | | 130 | | | | | 135 | | | | | 140 | |

| cag | gtg | gag | aac | tac | tat | agc | ctg | ccg | gga | cag | agc | tgc | tcg | gag | ccc | 603 |
|---|---|---|---|---|---|---|---|---|---|---|---|---|---|---|---|---|
| Gln | Val | Glu | Asn | Tyr | Tyr | Ser | Leu | Pro | Gly | Gln | Ser | Cys | Ser | Glu | Pro | |
| | | | | 145 | | | | | 150 | | | | | 155 | | |

| acc | agc | ccc | acc | tcc | aac | tgc | tct | gat | ggc | atg | ccc | gaa | tgt | aac | agt | 651 |
|---|---|---|---|---|---|---|---|---|---|---|---|---|---|---|---|---|
| Thr | Ser | Pro | Thr | Ser | Asn | Cys | Ser | Asp | Gly | Met | Pro | Glu | Cys | Asn | Ser | |
| | | 160 | | | | | 165 | | | | | 170 | | | | |

| cct | gtc | tgg | tcc | aga | aag | agc | agt | act | ttt | gac | agc | atc | tac | tgt | cct | 699 |
|---|---|---|---|---|---|---|---|---|---|---|---|---|---|---|---|---|
| Pro | Val | Trp | Ser | Arg | Lys | Ser | Ser | Thr | Phe | Asp | Ser | Ile | Tyr | Cys | Pro | |
| | | 175 | | | | | 180 | | | | | 185 | | | | |

| gat | gta | tca | aat | gta | tat | gcc | aca | gat | aaa | aac | tcc | tta | tcc | agc | ttg | 747 |
|---|---|---|---|---|---|---|---|---|---|---|---|---|---|---|---|---|
| Asp | Val | Ser | Asn | Val | Tyr | Ala | Thr | Asp | Lys | Asn | Ser | Leu | Ser | Ser | Leu | |
| | 190 | | | | | 195 | | | | | 200 | | | | | |

| gat | tgc | tta | tcc | aac | ata | gtg | gac | cgg | atc | acc | tcc | tca | gag | caa | cct | 795 |
|---|---|---|---|---|---|---|---|---|---|---|---|---|---|---|---|---|
| Asp | Cys | Leu | Ser | Asn | Ile | Val | Asp | Arg | Ile | Thr | Ser | Ser | Glu | Gln | Pro | |
| 205 | | | | | 210 | | | | | 215 | | | | | 220 | |

| ggg | ttg | cct | ctc | cag | gat | ctg | gct | tct | ctc | tct | cca | gtt | gcc | agc | acc | 843 |
|---|---|---|---|---|---|---|---|---|---|---|---|---|---|---|---|---|
| Gly | Leu | Pro | Leu | Gln | Asp | Leu | Ala | Ser | Leu | Ser | Pro | Val | Ala | Ser | Thr | |
| | | | | 225 | | | | | 230 | | | | | 235 | | |

| gat | tca | cag | cct | gca | act | cca | ggg | gct | tct | agt | tcc | agg | ctt | atc | tat | 891 |
|---|---|---|---|---|---|---|---|---|---|---|---|---|---|---|---|---|
| Asp | Ser | Gln | Pro | Ala | Thr | Pro | Gly | Ala | Ser | Ser | Ser | Arg | Leu | Ile | Tyr | |
| | | | 240 | | | | | 245 | | | | | 250 | | | |

| cat | gtg | cta | tga | actaattttc | tggtctatat | gacttcttcc | aggagggcct | 943 |
|---|---|---|---|---|---|---|---|---|
| His | Val | Leu | | | | | | |
| | | 255 | | | | | | | aatacacagg aagaagaagg cttcaaaaag tcccaaacca agacaacatg tacataaaga 1003 tttcttttca gttgtaaatt tgtaaagatt accttgccac tttataagaa agtgtattta 1063 actaaaaagt catcattgca aataatactt tcttcttctt tattattctt tgcttagata 1123 ttaatacata gttccagtaa tactatttct gataggggc cattgattga gggtagcttg 1183 ttgcaatgct taacttatat atacatatat atatattata aatattgctc atcaaaatgt 1243 ctctggtgtt tagagcttta ttttttcttt taaaacatta aaacagctga gaatcagtta 1303 aatggaattt taaatatatt taactatttc ttttctcttt aatccttag ttatattgta 1363 ttaaataaaa atataaatact gcctaatgta tatattttga tcttttcttg taagaaatgt 1423 atcttttaaa tgtaagcaca aaatagtact ttgtggatca tttcaagata taagaaattt 1483 tggaaattcc accataaata aaatttttta ctacaag 1520

<210> SEQ ID NO 4
<211> LENGTH: 255
<212> TYPE: PRT
<213> ORGANISM: Homo sapiens

<400> SEQUENCE: 4

| Met | Asp | Val | Met | Asp | Gly | Cys | Gln | Phe | Ser | Pro | Ser | Glu | Tyr | Phe | Tyr |
|---|---|---|---|---|---|---|---|---|---|---|---|---|---|---|---|
| 1 | | | | 5 | | | | | 10 | | | | | 15 | |

| Asp | Gly | Ser | Cys | Ile | Pro | Ser | Pro | Glu | Gly | Glu | Phe | Gly | Asp | Glu | Phe |
|---|---|---|---|---|---|---|---|---|---|---|---|---|---|---|---|
| | | | 20 | | | | | 25 | | | | | 30 | | |

| Val | Pro | Arg | Val | Ala | Ala | Phe | Gly | Ala | His | Lys | Ala | Glu | Leu | Gln | Gly |
|---|---|---|---|---|---|---|---|---|---|---|---|---|---|---|---|
| | | 35 | | | | | 40 | | | | | 45 | | | |

| Ser | Asp | Glu | Asp | Glu | His | Val | Arg | Ala | Pro | Thr | Gly | His | His | Gln | Ala |
|---|---|---|---|---|---|---|---|---|---|---|---|---|---|---|---|
| | 50 | | | | | 55 | | | | | 60 | | | | |

```
Gly His Cys Leu Met Trp Ala Cys Lys Ala Cys Arg Lys Ser Thr
 65                  70                  75                  80

Thr Met Asp Arg Arg Lys Ala Ala Thr Met Arg Glu Arg Arg Leu
                 85                  90                  95

Lys Lys Val Asn Gln Ala Phe Glu Thr Leu Lys Arg Cys Thr Thr Thr
            100                 105                 110

Asn Pro Asn Gln Arg Leu Pro Lys Val Glu Ile Leu Arg Asn Ala Ile
            115                 120                 125

Arg Tyr Ile Glu Ser Leu Gln Glu Leu Leu Arg Glu Gln Val Glu Asn
            130                 135                 140

Tyr Tyr Ser Leu Pro Gly Gln Ser Cys Ser Glu Pro Thr Ser Pro Thr
145                 150                 155                 160

Ser Asn Cys Ser Asp Gly Met Pro Glu Cys Asn Ser Pro Val Trp Ser
                165                 170                 175

Arg Lys Ser Ser Thr Phe Asp Ser Ile Tyr Cys Pro Asp Val Ser Asn
            180                 185                 190

Val Tyr Ala Thr Asp Lys Asn Ser Leu Ser Ser Leu Asp Cys Leu Ser
            195                 200                 205

Asn Ile Val Asp Arg Ile Thr Ser Ser Glu Gln Pro Gly Leu Pro Leu
210                 215                 220

Gln Asp Leu Ala Ser Leu Ser Pro Val Ala Ser Thr Asp Ser Gln Pro
225                 230                 235                 240

Ala Thr Pro Gly Ala Ser Ser Ser Arg Leu Ile Tyr His Val Leu
                245                 250                 255

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
caccatggag ctactgtcgc ca                                              22

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
tcagagcacc tggtatatcg ggt                                             23

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
caccatggac gtgatggatg gctg                                            24

<210> SEQ ID NO 8
<211> LENGTH: 20
<212> TYPE: DNA
<213> ORGANISM: Artificial Sequence
<220> FEATURE:
<223> OTHER INFORMATION: Primer
```

<400> SEQUENCE: 8
tcatagcaca tgatagataa                                              20

<210> SEQ ID NO 9
<211> LENGTH: 22
<212> TYPE: DNA
<213> ORGANISM: Artificial Sequence
<220> FEATURE:
<223> OTHER INFORMATION: Primer

<400> SEQUENCE: 9
caccatggag ctactgtcgc ca                                           22

<210> SEQ ID NO 10
<211> LENGTH: 23
<212> TYPE: DNA
<213> ORGANISM: Artificial Sequence
<220> FEATURE:
<223> OTHER INFORMATION: Primer

<400> SEQUENCE: 10
tcagagcacc tggtatatcg ggt                                          23

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
gactgccagc actttgctat ct                                           22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
cctcagagca cctggtatat cg                                           22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
caccatggac gtgatggatg gctg                                         24

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
tcatagcaca tgatagataa                                              20

<210> SEQ ID NO 15

```
<211> LENGTH: 20
<212> TYPE: DNA
<213> ORGANISM: Artificial Sequence
<220> FEATURE:
<223> OTHER INFORMATION: Primer

<400> SEQUENCE: 15
gcctgaagaa ggtcaaccag                                                      20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
attaggccct cctggaagaa                                                      20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgggcgtgta aggtgtgtaa                                                      20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
catggtttca tctgggaagg                                                      20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ctcttccagc cttccttcct                                                      20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
caccttcacc gttccagttt                                                      20

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
```

-continued

```
gcatctggca caatgacaac                                              20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
caccagctgc acctgttcta                                              20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
aacaaagctc aggtcggatt                                              20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
actggcatct gtttttgagg                                              20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
gacaggggga ggggaggagc tagg                                         24

<210> SEQ ID NO 26
<211> LENGTH: 26
<212> TYPE: DNA
<213> ORGANISM: Artificial Sequence
<220> FEATURE:
<223> OTHER INFORMATION: Primer

<400> SEQUENCE: 26
cttccctcca accagttgcc ccaaac                                       26

<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
cagccccgat tcttccacca gtccc                                        25

<210> SEQ ID NO 28
<211> LENGTH: 25
<212> TYPE: DNA
```

```
<213> ORGANISM: Artificial Sequence
<220> FEATURE:
<223> OTHER INFORMATION: Primer

<400> SEQUENCE: 28
cggaagattc ccagtcgggt tcacc                                           25

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
gggaaatggg agggtgcaa aagagg                                           26

<210> SEQ ID NO 30
<211> LENGTH: 26
<212> TYPE: DNA
<213> ORGANISM: Artificial Sequence
<220> FEATURE:
<223> OTHER INFORMATION: Primer

<400> SEQUENCE: 30
ttgcgtgagt gtggatggga ttggtg                                          26

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
ggatcactag gtgatatcga gc                                              22

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
accagacaag agtttaagag atatgtatc                                       29

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
catccccgac tacttgaagc                                                 20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
cccatggtct tcttctgcat                                                 20
```

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
cactccggtc ccaaatgtag                                          20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
ttccctgtag caccacacac                                          20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
acatggccaa ggtactgacc                                          20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgatggggtc aaagagttcc                                          20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gatgcacgaa tggatgacac                                          20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tgtgctacag gtggagcttg                                          20

<210> SEQ ID NO 41
<211> LENGTH: 22
<212> TYPE: DNA
<213> ORGANISM: Artificial Sequence
<220> FEATURE:

```
<223> OTHER INFORMATION: Primer

<400> SEQUENCE: 41
caccattggc aatgagcggt tc                                              22

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
aggtctttgc ggatgtccac gt                                              22
```

METHOD OF INDUCING DIFFERENTIATION FROM PLURIPOTENT STEM CELLS TO SKELETAL MUSCLE CELLS

CROSS-REFERENCE TO RELATED APPLICATIONS

This patent application is the U.S. national phase of International Patent Application No. PCT/JP2012/071373, filed Aug. 17, 2012, which claims the benefit of U.S. Provisional Patent Application No. 61/561,586, filed on Nov. 18, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 23,150 bytes ASCII (Text) file named "716802Sequence-Listing.txt," created May 13, 2014.

TECHNICAL FIELD OF THE INVENTION

The present invention relates to a method of inducing differentiation of pluripotent stem cells, particularly induced pluripotent stem cells, into skeletal muscle cells, a reagent kit to be used for said method, and skeletal muscle cells obtained by said method. The present invention also relates to a screening method of a therapeutic agent for myopathy using the aforementioned skeletal muscle cells.

BACKGROUND OF THE INVENTION

While muscle diseases include very many diseases, most of the symptoms thereof are muscle atrophy and muscle weakness associated therewith. The etiology of the muscle atrophy includes abnormality in the muscle itself and abnormality in the nerve that moves the muscle, where the former is called a muscle myogenic disease (myopathy), and the latter is called a neurogenic disease. The representative myopathy includes muscular dystrophy, muscular atrophy and the like. In Duchenne muscular dystrophy with the highest number of patients from among muscular dystrophies, one codon changes, by point mutation, to a stop codon meaning the termination of protein synthesis, due to which dystrophin protein is not synthesized. It is a disease developed only in boys by sex chromosome recessive inheritance, and said to be developed by 3 to 5 per 100,000 boys, and one per 2000-3000 newborn boys. There is not any good treatment method for muscular dystrophy, and the development of a treatment method has been desired. Miyoshi myopathy (MM) is one of the congenital distal myopathy (Miyoshi, K. et al. Brain 109 (Pt 1), 31-54, 1986), and caused by defective muscle membrane repair due to mutated Dysferlin (Liu, J. et al. Nat Genet. 20, 31-36, 1998, and Bansal, D., et al. Nature 423, 168-172, 2003).

For the development of a therapeutic drug, a model reflecting the human pathology in vitro is required. With the development of an induced pluripotent stem cell by reprogramming a somatic cell in recent years, utilization of a cell generated from patient's own cell as a pathology model is expected. While there are some reports on the method of inducing skeletal muscle cells from human pluripotent stem cells (Zheng, J. K. et al., Cell Res., 16: 713-22, 2006, Barberi, T. et al., Nat. Med., 13: 642-8, 2007), a method of efficiently inducing a cell in the number necessary for the development of a therapeutic drug has not been reported yet.

Directed differentiation by driving master transcriptional factor, MyoD1, from adult somatic cells was initially established for myogenic differentiation in 1988 (Tapscott, S. J., et al. Science 242, 405-411, 1988). Various types of cells can give rise to myocytes driven by forced expression of MyoD1 (Mizuno, H., et al. Plastic and reconstructive surgery 109, 199-209, 2002, and Gianakopoulos, P. J., et al. The Journal of biological chemistry 286, 2517-2525, 2011). In pluripotent stem cells, mouse embryonic stem cells can differentiate to myocytes by Tetracycline (Tet)-inducible MyoD1 expression (Ozasa, S., et al. Biochemical and biophysical research communications 357, 957-963, 2007), and hiPSC-derived fibroblasts can also differentiate to myocytes by MyoD1 mRNA treatment after differentiation under the condition without FGF for 4 weeks (Warren, L., et al. Cell stem cell 7, 618-630, 2010).

SUMMARY OF THE INVENTION

An object of the present invention is to provide a method of inducing differentiation of pluripotent stem cells including iPS cells into skeletal muscle cells, and a differentiation-inducing reagent kit containing a gene transiently introduced in said method. A further object of the present invention is to provide a means for screening for a therapeutic agent for muscle diseases such as myopathies including muscular dystrophy, Miyoshi myopathy and the like, which uses a skeletal muscle cell derived from a pluripotent stem cell obtained by said method.

Heretofore, attempts have been made to induce skeletal muscle cells by inducing differentiation of pluripotent stem cell to some extent by forming embryoid and the like, and introducing an exogenous gene into a cell appropriately expressing an endogenous gene (Darabi, R. et al., Nat. Med., 14, 134-143, 2008).

Thus, the present inventors have considered from a different angle, and found for the first time that differentiation of pluripotent stem cells, which were cultured under conditions that do not specifically induce skeletal muscle cell, into skeletal muscle cells can be unexpectedly induced efficiently and quickly by expressing exogenous MyoD and adjusting the expression period thereof. Furthermore, they have found that a similar effect can also be achieved by introducing Myf5 in the same manner.

They have therefore considered that a sufficient number of disease specific skeletal muscle cells can be obtained by inducing skeletal muscle cells by these methods by using induced pluripotent stem cells derived from myopathy patients, and that the cells can be used for screening of a therapeutic drug for said pathology, which resulted in the completion of the present invention.

Accordingly, the present invention provides the following.

[1] A method of producing a skeletal muscle cell from a pluripotent stem cell, comprising a step of expressing one or more exogenous factors selected from MyoD, Myf5 and nucleic acids encoding them in the pluripotent stem cell.
[2] The method of [1], wherein the pluripotent stem cell is human pluripotent stem cell.
[3] The method of [1] or [2], wherein the exogenous factor is expressed in the pluripotent stem cell within 3 days from the start of culture under differentiation inducing conditions.

[4] The method of [3], wherein the exogenous factor is expressed in the pluripotent stem cell within 1 day from the start of culture under differentiation inducing conditions.
[5] The method of [3], wherein the differentiation inducing conditions do not involve a step which an embryoid body is formed.
[6] The method of [3], wherein the differentiation inducing conditions include culturing in a bFGF-free basal medium containing a serum or a serum substitute.
[7] The method of any of [1] to [6], comprising a step of further culturing in a culture medium containing horse serum, after expression of the exogenous factor.
[8] The method of any of [1] to [7], wherein the expression of the exogenous factor is maintained for not less than 5 days and not more than 10 days.
[9] The method of any of [1] to [8], wherein the expression of the exogenous factor in the pluripotent stem cell is performed by culturing a pluripotent stem cell introduced with a drug responsive inducible vector containing a nucleic acid encoding MyoD or Myf5, in the presence of said drug.
[10] A composition for differentiation induction of a pluripotent stem cell into a skeletal muscle cell, comprising one or more factors selected from MyoD, Myf5 and nucleic acids encoding them.
[11] The composition of [10], wherein the factor is a drug responsive inducible vector containing a nucleic acid encoding MyoD or Myf5.
[12] The composition of [10], wherein the pluripotent stem cell is a human pluripotent stem cell.
[13] A kit for inducing a skeletal muscle cell from a pluripotent stem cell, comprising one or more factors selected from MyoD, Myf5 and nucleic acids encoding them.
[14] The kit of [13], comprising a drug responsive inducible vector containing a nucleic acid encoding MyoD or Myf5.
[15] A method of screening for an agent for the treatment or prophylaxis of myopathy, comprising using the skeletal muscle cell produced by the method of any of [1] to [9].
[16] A pluripotent stem cell having a drug responsive inducible vector containing a nucleic acid encoding MyoD or Myf5.

According to the present invention, the differentiation of a pluripotent stem cell to a skeletal muscle cell can be efficiently induced by transiently expressing exogenous MyoD or Myf5 in the pluripotent stem cell. According to the present invention, moreover, differentiation of an iPS cell to a skeletal muscle cell can be induced, and therefore, skeletal muscle cells can be stably supplied without an ethical limitation as in ES cells. Furthermore, using a skeletal muscle cell induced from an iPS cell established from a patient having a target disease, a disease model cell can be easily obtained, which can be applied to the use for screening for an agent for the treatment or prophylaxis of said disease.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2a shows the protocol of the skeletal muscle cell induction using an SB outgrowth method and MyoD induction expression in combination. In the Figure, ① means that SB outgrowth cells (SB-OG) were cultured in an SB outgrowth medium with or without Dox addition for 4 days, and thereafter cultured in a DMEM medium containing 2% horse serum and IGF-1 for 3 days, ② means that the cells were cultured in an SB outgrowth medium with or without Dox addition for 5 days, and thereafter cultured in a DMEM medium containing 2% horse serum and IGF-1 for 2 days, ③ means that the cells were cultured in an SB outgrowth medium with or without Dox addition for 6 days, and thereafter cultured in a DMEM medium containing 2% horse serum and IGF-1 for 1 day, and ④ means that the cells were cultured in an SB outgrowth medium with or without Dox addition for 7 days. FIG. 2b shows immunostained images with an anti-MHC antibody of the cells of Dox addition group (Dox(+)) and non-addition group (Dox(−)), using the culture protocol of ③. In the Figure, arrows show matured skeletal muscle cells. FIG. 2c is a graph showing the MHC positive cell number under the respective culture conditions shown in FIG. 2a. FIG. 2d shows the protocol of skeletal muscle cell induction using a paraxial mesoderm induction method and MyoD induction expression in combination. FIG. 2e shows fluorescence microscope images and anti-MHC antibody-stained images of the cells of the Dox addition group (Dox(+)) and non-addition group (Dox (−)) when a paraxial mesoderm induction method is used.

In FIG. 11e, human Spectrin expression (red) was detected along with Laminin (green). Scale bars show 20 µm. In FIG. 11f, human Dystrophin expression (green) was detected along with Laminin (white). Scale bars show 20 µm.

DETAILED DESCRIPTION OF THE INVENTION

Figure 1:
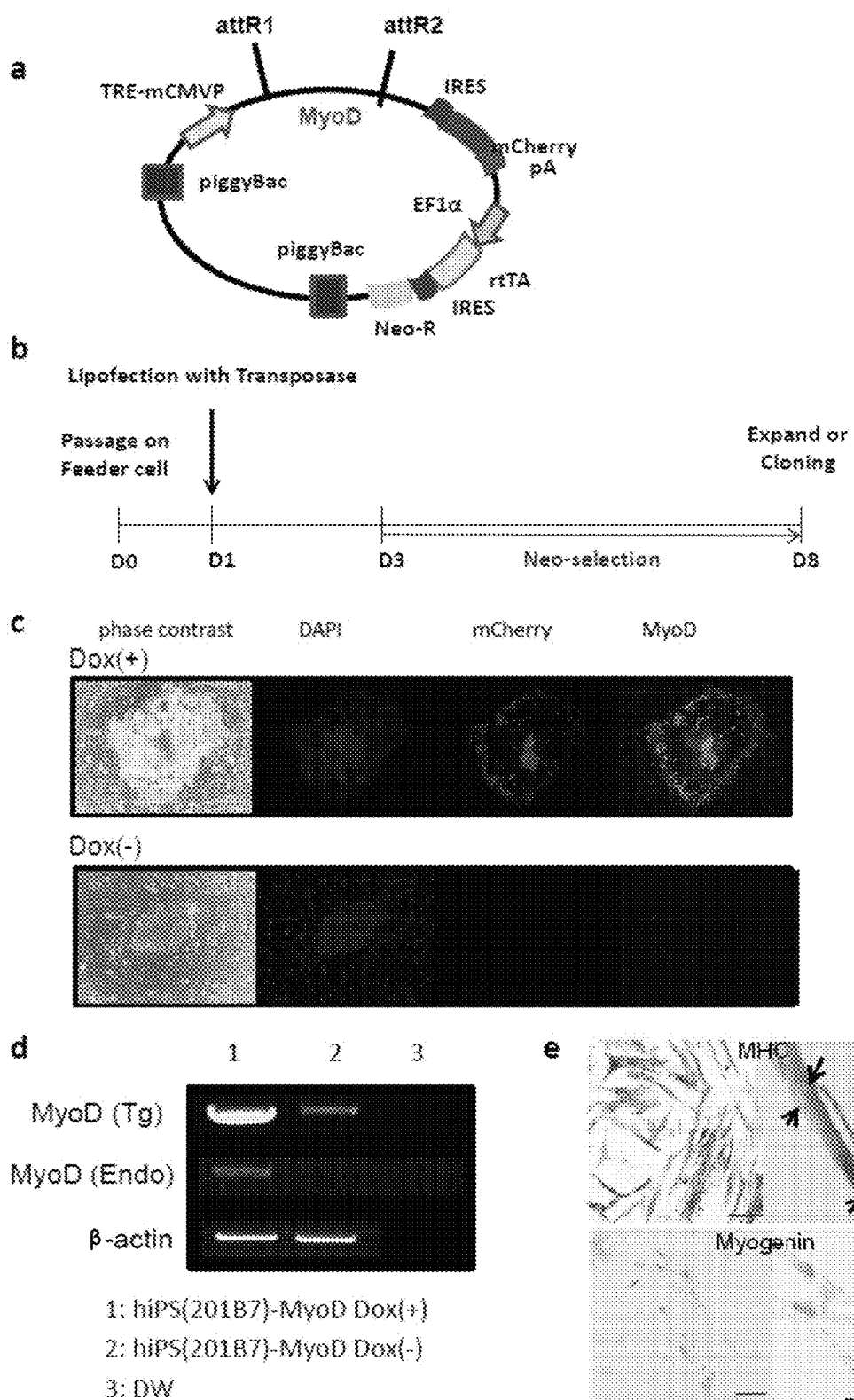
FIG. 1a shows the structure of tetracycline responsive MyoD expression piggyBac vector.
FIG. 1b shows the transformation protocol of iPS cell. In the Figure, D1 means day 1 after passage culture. On D1, transposase expression vector and tetracycline responsive MyoD expression piggyBac vector were introduced into the cell by lipofection. On D8, expanded culture or cloning was performed.
FIG. 1c shows (from the left) phase contrast microscope image, fluorescence microscope image after DAPI staining, fluorescence microscope image showing expression of mCherry and fluorescence microscope image after immunofluorescence staining with anti-MyoD antibody, of the addition group (Dox(+)) at 48 hr after Doxycyclin (Dox) addition to neomycin resistant cell and non-addition group (Dox(−)).
FIG. 1d shows the expression levels of exogeneous MyoD (MyoD(Tg)) and endogenous MyoD (MyoD(Endo)) in the cells of the addition group (lane 1) at 48 hr after Dox addition and non-addition group (lane 2), which results were confirmed by PCR.
FIG. 1e shows immunostained images of MHC and myogenin in transfected human iPS cell clone after Dox addition. Arrows indicate nuclei. Scale bars show 100 μm.

The present invention provides a method of producing a skeletal muscle cell from a pluripotent stem cell. This method contains a step of expressing one or more exogenous factors selected from MyoD, Myf5 and nucleic acids encoding them (hereinafter to be also referred to as "the skeletal muscle cell inducer of the present invention") in the pluripotent stem cell.

In the present invention, production of skeletal muscle cell only means obtaining cell population containing a skeletal muscle cell. Preferably, it means to obtain a cell population containing the skeletal muscle cells in a proportion of not less than 50%, 60%, 70%, 80% or 90%. The skeletal muscle cell is defined to mean a cell expressing a marker gene of skeletal muscle cells such as Myogenin, myosin heavy chain (MHC) and the like, and may be a polynuclear cell or a mononuclear cell.

As the skeletal muscle cell inducer of the present invention, for example, an MyoD or Myf5 protein derived from any mammal (e.g., human, mouse, rat, monkey, bovine, horse, swine, dog etc.) or a nucleic acid encoding the same and the like can be used. A species of the same derivation as the target pluripotent stem cell is preferable.

Examples of the MyoD to be used in the present invention include human myogenic differentiation 1 (MYOD1) consisting of the amino acid sequence shown by SEQ ID NO: 2 (registered as NCBI accession number: NP_002469), and an ortholog thereof in other mammal, a transcription variant thereof, a splicing variant thereof and the like. Alternatively, it may be a protein having an amino acid identity of not less than 90%, preferably not less than 95%, more preferably not less than 97%, with any of the above-mentioned proteins, and having a function equivalent to that of said protein (e.g., transcription activation of muscle specific promoter and the like). The identity of the amino acid sequence as mentioned herein can be calculated using the blastp program of the NCBI BLAST (National Center for Biotechnology Information Basic Local Alignment Search Tool) under the following conditions (expectancy=10; gap allowed; matrix=BLOSUM62; filtering=OFF).

Examples of Myf5 to be used in the present invention include human myogenic factor 5 (MYF5) consisting of the amino acid sequence shown by SEQ ID NO: 4 (registered as NCBI accession number: NP_005584), and an ortholog thereof in other mammal, a transcription variant thereof, a splicing variant thereof and the like. Alternatively, it may be a protein having an amino acid identity of not less than 90%, preferably not less than 95%, more preferably not less than 97%, with any of the above-mentioned proteins, and having a function equivalent to that of said protein (e.g., transcription activation of muscle specific promoter and the like).

Here, the identity of the amino acid sequence can be calculated in the same manner as in the above.

MyoD and Myf5 may be a fusion protein of any of the above-mentioned proteins and a cell penetrating peptide (e.g., TAT derived from HIV and polyarginine).

Examples of the nucleic acid encoding MyoD include human myogenic differentiation 1 (MYOD1) cDNA consisting of the nucleotide sequence shown by SEQ ID NO: 1 (registered as NCBI accession number: NP_002478), and an ortholog thereof in other mammal, a transcription variant thereof, a splicing variant thereof and the like. Alternatively, it may be a nucleic acid encoding a protein having a nucleotide identity of not less than 90%, preferably not less than 95%, more preferably not less than 97%, with any of the above-mentioned nucleic acids, and having a function equivalent to that of a protein encoded by said nucleic acid (e.g., transcription activation of muscle specific promoter and the like). The identity of the nucleotide sequence as mentioned herein can be calculated using the blastn program of the NCBI BLAST (National Center for Biotechnology Information Basic Local Alignment Search Tool) under the following conditions (expectancy=10; gap allowed; filtering=ON; match score=1; mismatch score=−3). Alternatively, it may have a plus strand in a complementary relationship of the level permitting hybridization with the complementary strand of any of the above-mentioned nucleic acids under stringent conditions. The stringent conditions herein can be determined based on the melting temperature (Tm) of the nucleic acid binding to a complex or probe, as taught in Berger and Kimmel (1987, Guide to Molecular Cloning Techniques Methods in Enzymology, Vol. 152, Academic Press, San Diego Calif.). For example, wash conditions after hybridization generally include about "1×SSC, 0.1% SDS, 37° C.". The complementary strand is preferably one that maintains hybridization state with the target plus strand even when washed under such conditions. Although not particularly limited, more stringent hybridization conditions include wash conditions of about "0.5×SSC, 0.1% SDS, 42° C.", more stringent wash conditions of about "0.1×SSC, 0.1% SDS, 65° C.", which permit the plus strand and the complementary strand to maintain hybridization state even after washing.

Examples of the nucleic acid encoding Myf5 include human myogenic factor 5 (MYF5) cDNA consisting of the nucleotide sequence shown by SEQ ID NO: 3 (registered as NCBI accession number: NM_005593), and an ortholog thereof in other mammal, a transcription variant thereof, a splicing variant thereof and the like. Alternatively, it may be a nucleic acid encoding a protein having a nucleotide identity of not less than 90%, preferably not less than 95%, more preferably not less than 97%, with any of the above-mentioned nucleic acids, and having a function equivalent to that of a protein encoded by said nucleic acid (e.g., transcription activation of muscle specific promoter and the like). The identity of the nucleotide sequence as mentioned herein can be calculated in the same manner as mentioned above. Alternatively, it may have a plus strand in a complementary relationship of the level permitting hybridization with the complementary strand of any of the above-mentioned nucleic acids under stringent conditions. The stringent conditions as mentioned herein are as defined above.

The nucleic acid encoding MyoD or Myf5 may be DNA, RNA or DNA/RNA chimera. In addition, the nucleic acid may be a single strand, double stranded DNA, double stranded RNA or DNA:RNA hybrid. Preferred is a double stranded DNA or single stranded RNA. As said RNA, RNA incorporating 5-methylcytidine and pseudouridine (TriLink Biotechnologies), or a modified RNA obtained by a phosphatase treatment may be used for the suppression of degradation.

MyoD and Myf5, and nucleic acids encoding them can be obtained by easily isolating a nucleic acid encoding each protein or, where necessary, producing a recombinant protein or chemically synthesizing the same based on, for example, the cDNA sequence information of the above-mentioned human MYOD1 and human Myf5.

<Pluripotent Stem Cell>

When a cell population containing a skeletal muscle cell is prepared by differentiating a pluripotent stem cell, a usable pluripotent stem cell is a stem cell having pluripotency permitting differentiation into any cell present in living organisms, and also having proliferation potency. While it is not particularly limited, it includes, for example, embryonic stem (ES) cell, embryonic stem cell derived from a cloned embryo obtained by nuclear transplantation (ntES cell), germline stem cell ("GS cell"), embryonic germ cell ("EG cell"), induced pluripotent stem (iPS) cell, cultured fibroblast- or myeloid stem cell-derived pluripotent cell (Muse cell) and the like. Preferable pluripotent stem cells are ES cell, ntES cell and iPS cell.

(A) Embryonic Stem Cell

ES cell is a stem cell having pluripotency and proliferation potency based on self-renewal, which is established from an inner cell mass of an early-stage embryo (for example, blastocyst) of a mammal such as human, mouse and the like.

ES cell is an embryo-derived stem cell derived from an inner cell mass of blastocyst, which is an embryo after morula at 8-cell stage of a fertilized egg, and has an ability to differentiate into any cell constituting an adult body, i.e., pluripotent differentiation potency, and proliferation potency based on self-renewal. The ES cell was discovered in mouse in 1981 (M. J. Evans and M. H. Kaufman (1981), Nature 292:154-156) and thereafter ES cell lines were also established in primates such as human, monkey and the like (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38:133-165).

ES cell can be established by removing an inner cell mass from the blastocyst of a fertilized egg of a target animal, and culturing the inner cell mass on fibroblast feeder cells. In addition, the cells can be maintained by passage culture using a culture medium added with substances such as leukemia inhibitory factor (LIF), basic fibroblast growth factor (bFGF) and the like. The methods of establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485 and the like.

Using, as a culture medium for preparing ES cells, for example, a DMEM/F-12 culture medium supplemented with 0.1 mM 2-mercaptoethanol, 0.1 mM nonessential amino acids, 2 mM L-glutamic acid, 20% KSR and 4 ng/ml bFGF, human ES cells can be maintained under wet atmosphere at 37° C., 2% $CO_2$/98% air (O. Fumitaka et al. (2008), Nat. Biotechnol., 26:215-224). In addition, ES cells require passage every 3-4 days, and the passage in this case can be performed using, for example, 0.25% trypsin and 0.1 mg/ml collagenase IV in PBS containing 1 mM $CaCl_2$ and 20% KSR.

ES cells can be generally selected by the Real-Time PCR method using the expression of a gene marker such as alkaline phosphatase, Oct-3/4, Nanog and the like as an index. Particularly, for selection of human ES cell, expression of a gene marker such as OCT-3/4, NANOG, ECAD and the like can be used as an index (E. Kroon et al. (2008), Nat. Biotechnol., 26:443-452).

As for human ES cell line, for example, WA01(H1) and WA09(H9) are available from WiCell Research Institute, and KhES-1, KhES-2 and KhES-3 are available from Institute for Frontier Medical Sciences, Kyoto University (Kyoto, Japan).

(B) Germline Stem Cell

Germline stem cell is a pluripotent stem cell derived from the testis, which becomes the origin for spermatogenesis. This cell can be differentiation induced into various lines of cells, like ES cells and shows properties of, for example, generation of a chimeric mouse by transplantation into a mouse blastocyst and the like (M. Kanatsu-Shinohara et al. (2003) Biol. Reprod., 69:612-616; K. Shinohara et al. (2004), Cell, 119:1001-1012). It is self-renewable in a culture medium containing a glial cell line-derived neurotrophic factor (GDNF), can produce a germline stem cell by repeating passages under culture conditions similar to those for ES cells (Masanori Takehashi et al., (2008), Experimental Medicine, Vol. 26, No. 5 (Suppl.), pp. 41-46, YODOSHA (Tokyo, Japan)).

(C) Embryonic Germ Cell

Embryonic germ cell is a cell having pluripotency similar to that of ES cells, which is established from a primordial germ cell at the prenatal period. It can be established by culturing a primordial germ cell in the presence of a substance such as LIF, bFGF, a stem cell factor and the like (Y. Matsui et al. (1992), Cell, 70:841-847; J. L. Resnick et al. (1992), Nature, 359:550-551).

(D) Induced Pluripotent Stem Cell

Induced pluripotent stem (iPS) cell is an artificial stem cell derived from a somatic cell, which can be produced by introducing a specific reprogramming factor in the form of a DNA or protein into a somatic cell, and show almost equivalent property (e.g., pluripotent differentiation and proliferation potency based on self-renewal) as ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO2007/069666). The reprogramming factor may be constituted with a gene specifically expressed by ES cell, a gene product or non-coding RNA thereof, a gene playing an important role for the maintenance of undifferentiation of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1 and the like. These reprogramming factors may be used alone or in combination. Examples of the combination of the reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat. Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

Examples of the above-mentioned reprogramming factor include, but are not limited to, factors used for enhancing the establishment efficiency, such as histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (for example, Bayk8644), butyric acid, TGFβ inhibitor or ALK5 inhibitor (e.g., LY364947, SB431542, 616453 and A-83-01), p53 inhibitor (for example, siRNA and shRNA against p53), ARID3A inhibitor (e.g., siRNA and shRNA against ARID3A), miRNA such as miR-291-3p, miR-294, miR-295, mir-302 and the like, Wnt Signaling (for example, soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. In the present specification, these factors used for enhancing the establishment efficiency are not particularly distinguished from the reprogramming factor.

When the reprogramming factor is in the form of a protein, it may be introduced into a somatic cell by a method, for example, lipofection, fusion with cell penetrating peptide (e.g., TAT derived from HIV and polyarginine), microinjection and the like.

When the reprogramming factor is in the form of a DNA, it may be introduced into a somatic cell by the method using, for example, vector of virus, plasmid, artificial chromosome and the like, lipofection, liposome, microinjection and the like. Examples of the virus vector include retrovirus vector, lentivirus vector (Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, Sendai virus vector (vector of Hemagglutinating Virus of Japan) (WO 2010/008054) and the like. Examples of the artificial chromosome vector include human artificial chromosome (HAC), yeast artificial chromosome (YAC), bacterial artificial chromosome (BAC, PAC) and the like. As the plasmid, plasmids for mammalian cells can be used (Science, 322:949-953, 2008). The vector can contain regulatory sequences of promoter, enhancer, ribosome binding sequence, terminator, polyadenylation site and the like so that a nuclear reprogramming substance can be expressed and further, where necessary, a selection marker sequence of a drug resistance gene (for example, kanamycin resistance gene, ampicillin resistance gene, puromycin resistance gene and the like), thymidine kinase gene, diphtheria toxin gene and the like, a reporter gene sequence of green fluorescent protein (GFP), β glucuronidase (GUS), FLAG and the like, and the like. Moreover, the above-mentioned vector may have a LoxP sequence before and after thereof to simultaneously cut out a gene encoding a reprogramming factor or a gene encoding a reprogramming factor bound to the promoter, after introduction into a somatic cell.

When in the form of RNA, for example, it may be introduced into a somatic cell by means of lipofection, microinjection and the like, and RNA incorporating 5-methylcytidine and pseudouridine (TriLink Biotechnologies) may be used to suppress degradation (Warren L, (2010) Cell Stem Cell. 7:618-630).

Examples of the culture medium for inducing iPS cell include 10-15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for mouse ES cell culture (TX-WES culture medium, Thromb-X), culture medium for primate ES cell (culture medium for primate ES/iPS cell, Reprocell), serum-free medium (mTeSR, Stemcell Technologies)] and the like.

Examples of the culture method include contacting a somatic cell with a reprogramming factor on 10% FBS-containing DMEM or DMEM/F12 culture medium at 37° C. in the presence of 5% $CO_2$ and culturing for about 2-7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby iPS-like colonies can be obtained after about 30-about 45 days or longer from the contact.

Alternatively, the cells are cultured on feeder cells (e.g., mitomycin C-treated STO cells, SNL cells etc.) at 37° C. in the presence of 5% $CO_2$ in a 10% FBS-containing DMEM culture medium (which can further contain LIF, penicillin/streptomycin, puromycin, L-glutamine, nonessential amino acids, β-mercaptoethanol and the like as appropriate), whereby ES-like colonies can be obtained after about 25-about 30 days or longer. Desirably, a method using a somatic cell itself to be reprogrammed, or an extracellular substrate (e.g., Laminin-5 (WO2009/123349) and Matrigel (BD)), instead of the feeder cells (Takahashi K, et al. (2009), PLoS One. 4:e8067 or WO2010/137746), can be mentioned.

Besides the above, a culture method using a serum-free medium can also be recited as an example (Sun N, et al. (2009), Proc Natl Acad Sci USA. 106:15720-15725). Furthermore, to enhance establishment efficiency, an iPS cell may be established under hypoxic conditions (oxygen concentration of not less than 0.1% and not more than 15%) (Yoshida Y, et al. (2009), Cell Stem Cell. 5:237-241 or WO2010/013845).

The culture medium is exchanged with a fresh culture medium once a day during the above-mentioned cultures, from day 2 from the start of the culture. While the cell number of the somatic cells used for nuclear reprogramming is not limited, it is about 5×10³-about 5×10⁶ cells per 100 cm² culture dish.

The iPS cell can be selected based on the shape of the formed colony. When a drug resistance gene which is expressed in association with a gene (e.g., Oct3/4, Nanog) expressed when a somatic cell is reprogrammed is introduced as a marker gene, an established iPS cell can be selected by culturing in a culture medium (selection culture medium) containing a corresponding drug. When the marker gene is a fluorescent protein gene, iPS cell can be selected by observation with a fluorescence microscope, when it is a luminescent enzyme gene, iPS cell can be selected by adding a luminescent substrate, and when it is a chromogenic enzyme gene, iPS cell can be selected by adding a chromogenic substrate.

The term "somatic cell" used in the present specification means any animal cell (preferably, cells of mammals inclusive of human) excluding germ line cells and totipotent cells such as ovum, oocyte, ES cells and the like. Somatic cell unlimitatively encompasses any of somatic cells of fetuses, somatic cells of neonates, and mature healthy or pathogenic somatic cells, and any of primary cultured cells, passage cells, and established lines of cells. Specific examples of the somatic cell include (1) tissue stem cells (somatic stem cells) such as neural stem cell, hematopoietic stem cell, mesenchymal stem cell, dental pulp stem cell and the like, (2) tissue progenitor cell, (3) differentiated cells such as lymphocyte, epithelial cell, endothelial cell, myocyte, fibroblast (skin cells etc.), hair cell, hepatocyte, gastric mucosal cell, enterocyte, splenocyte, pancreatic cell (pancreatic exocrine cell etc.), brain cell, lung cell, renal cell and adipocyte and the like, and the like.

When iPS cell is used as a material for transplantation cell, a somatic cell having the same or substantially the same HLA genotype as the individual receiving the transplantation is desirably used since rejection does not occur. Being "substantially the same" here means that the HLA genotype is the same to the extent the immune reaction against the transplanted cell can be suppressed by an immunosuppressant. For example, it is a somatic cell having an HLA type showing a match of 3 gene loci of HLA-A, HLA-B and HLA-DR or 4 gene loci additionally with HLA-C.

(E) ES Cells Derived from Cloned Embryo by Nuclear Transplantation nt ES cell is an ES cell derived from a cloned embryo prepared by a nuclear transplantation technique, and has almost the same property as the ES cell derived from a fertilized egg (T. Wakayama et al. (2001), Science, 292:740-743; S. Wakayama et al. (2005), Biol. Reprod., 72:932-936; J. Byrne et al. (2007), Nature, 450:497-502). That is, an ES cell established from an inner cell mass of a blastocyst derived from a cloned embryo obtained by substituting the nucleus of an unfertilized egg with the nucleus of a somatic cell is an nt ES (nuclear transfer ES) cell. For production of an nt ES cell, a combination of the nuclear transplantation technique (J. B. Cibelli et al. (1998), Nature Biotechnol., 16:642-646) and the ES cell production technique (mentioned above) is used (Kiyoka Wakayama et al., (2008), Experimental Medicine, Vol. 26, No. 5 (Suppl.), pp. 47-52). In nuclear transplantation, reprogramming can be performed by injecting the nucleus of a somatic cell to an enucleated unfertilized egg of a mammal, and culturing for a few hours.

(F) Multilineage-Differentiating Stress Enduring Cell (Muse Cell)

Muse cell is a pluripotent stem cell produced by the method described in WO2011/007900. In more detail, it is a cell having pluripotency, which is obtained by subjecting a fibroblast or a bone marrow stromal cell to a trypsin treatment for a long time, preferably 8 hr or 16 hr, and thereafter culturing the cells in a suspended state, and positive for SSEA-3 and CD105.

<Method of Producing Skeletal Muscle Cell from Pluripotent Stem Cell>

While the method of expressing a skeletal muscle cell inducer in the present invention in a pluripotent stem cell is not particularly limited, for example, the following method can be used. Here, "expression" means that, when the skeletal muscle cell inducer is a nucleic acid encoding MyoD or Myf5, an MyoD or Myf5 protein is produced by intracellular (transcription and) translation from the nucleic acid, and when the skeletal muscle cell inducer is a MyoD or Myf5 protein, it means the same as an intracellular introduction of the protein.

When the aforementioned skeletal muscle cell inducer is in the form of a DNA, for example, a vector of virus, plasmid, artificial chromosome and the like may be introduced into a pluripotent stem cell by a method such as lipofection, liposome, microinjection and the like. Examples of the virus vector include retrovirus vector, lentivirus vector, adenovirus vector, adeno-associated virus vector, Sendai virus vector and the like. Examples of the artificial chromosome vector include human artificial chromosome (HAC), yeast artificial chromosome (YAC), bacterial artificial chromosome (BAC, PAC) and the like. Examples of the plasmid include plasmids for mammalian cells. The vector can contain regulatory sequences of promoter, enhancer, ribosome binding sequence, terminator, polyadenylation site and the like so that a DNA encoding MyoD or Myf5 can be expressed and further, where necessary, selection marker sequences of a drug resistance gene (for example, kanamycin resistance gene, ampicillin resistance gene, puromycin resistance gene and the like), thymidine kinase gene, diphtheria toxin gene and the like, a reporter gene sequence of fluorescent protein, β glucuronidase (GUS), FLAG and the like, and the like. As a promoter, SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter, EF-α promoter, CAG promoter and TRE promoter (minimal CMV promoter having a Tet response element with continuous 7 tetO sequences). When a TRE promoter is used, a fusion protein of tetR and VP16AD or a fusion protein of reverse tetR (rtetR) and VP16AD is desirably expressed simultaneously in the same cell. Here, a vector having a TRE promoter and capable of expressing a fusion protein of reverse tetR (rtetR) and VP16AD is referred to as a drug responsive inducible vector. In addition, to introduce an expression cassette consisting of a promoter and a DNA encoding MyoD or Myf5 bonded thereto into a chromosome of a pluripotent stem cell and cut it out as necessary therefrom, the above-mentioned vector may have a transposon sequence before and after the expression cassette. While the transposon sequence is not particularly limited, piggyBac can be mentioned. In another embodiment, it may have a LoxP sequence before and after the expression cassette to remove the expression cassette.

When the aforementioned skeletal muscle cell inducer is in the form of an RNA, it may be introduced into a pluripotent stem cell by a method such as electroporation, lipofection, microinjection and the like. When the inducer is in the form of a protein, it may be introduced into a pluripotent stem cell by a method such as lipofection, fusion with cell penetrating peptide (e.g., TAT derived from HIV and polyarginine), microinjection and the like.

An exogenous skeletal muscle cell inducer may be expressed in a pluripotent stem cell immediately after the start of the culture of the pluripotent stem cell under differentiation inducing conditions, or desirably at least within 3 days from the start of the culture, more desirably within 1 day from the start of the culture. When a skeletal muscle cell inducer is expressed after 3 days from the start of the culture under differentiation inducing conditions, for example, 4 to 7 days later, the differentiation efficiency into a skeletal muscle cell may decrease. While the period when the expression of an exogenous skeletal muscle cell inducer is maintained is not particularly limited, it is desirably not less than 5 days and preferably not more than 10 days (e.g., 5, 6, 7, 8, 9 or 10 days), more preferably 6 days. While the method of maintaining the expression is not particularly limited, when the skeletal muscle cell inducer is RNA or protein, the introduction can be performed plural times during a desired period. In another embodiment, when a drug responsive inducible vector is used, a method of maintaining expression by addition of doxycycline to the medium during a desired period; when a vector having a transposon sequence is used, a method including, after lapse of a desired period, intracellularly introducing transposase to discontinue expression; and when a vector having a LoxP sequence is used, a method including, after lapse of a desired period, intracellularly introducing Cre to discontinue expression and the like can be recited as examples.

In the present invention, the differentiation inducing conditions for pluripotent stem cell are adhesion culture conditions that do not allow formation of embryoid and are not induction conditions for a particular cell type. For example, they are culture conditions for adhesion to a coating-treated culture dish by using Matrigel (BD), Type I collagen, Type IV collagen, gelatin, laminin, heparan sulfate proteoglycan, or entactin, and a combination of these, and in a medium used for the culture of animal cells as a basal medium, which is added with a serum or a serum substitute. In this case, the medium is desirably free of bFGF. Here, examples of the basal medium include GMEM (Glasgow Minimum Essential Medium), IMDM (Iscove's Modified Dulbecco's Medium), Medium 199, Eagle's Minimum Essential Medium (EMEM), αMEM, Dulbecco's modified Eagle's Medium (DMEM), Ham's F12 medium, RPMI 1640 medium, Fischer's medium, and a combined medium thereof and the like. Examples of the serum substitute include albumin, transferrin, fatty acid, insulin, collagen precursor, trace element, Knockout Serum Replacement (KSR) (serum substitute of FBS for ES cells culture), ITS-supplement and mixtures thereof and the like.

The differentiation inducing conditions of the present invention may be free from induction of a skeletal muscle cell when a skeletal muscle cell inducer is not introduced.

Preferable differentiation inducing conditions are those for culturing pluripotent stem cells adhered to a culture dish coated with Matrigel in a mixed medium of equal amounts of DMEM and F12, which contains 20% KSR, transferring the cells to a culture dish coated with Type I collagen, and culturing in an αMEM medium containing 5% KSR.

In the another embodiment, preferable differentiation inducing conditions are those for culturing pluripotent stem cells adhered to a culture dish coated with Matrigel or collagen type I in a mixed medium of equal amounts of DMEM and F12, which contains 20% KSR. After 1 day from induction of a skeletal muscle cell inducer, culture medium was changed to alpha Minimal Essential Medium (αMEM) with 5% Knockout Serum Replacement (KSR), and 100 μM 2-Mercaptoethanol (2-ME).

To further mature the produced skeletal muscle cells, following the expression of the skeletal muscle cell inducer under the above-mentioned differentiation inducing conditions, the culture is preferably continued in a DMEM medium added with 5% horse serum (HS) for 1, 2 or 3 days, preferably 2 days. In this case, IGF-1 may be contained.

While the incubation temperature is not particularly limited, it is about 30-40° C., preferably about 37° C., and the culture is performed under the atmosphere of $CO_2$ containing air, where the $CO_2$ concentration is preferably about 2-5%.

The thus-produced cell population containing a skeletal muscle cell may not be a single cell population but a cell population containing other kinds of cells.

<Kit for Production of Skeletal Muscle Cell from Pluripotent Stem Cell>

The present invention provides a kit for production of a skeletal muscle cell from a pluripotent stem cell. The kit can contain the aforementioned skeletal muscle cell inducer of the present invention, i.e., a skeletal muscle cell inducer containing one or more factors selected from MyoD, Myf5 and nucleic acids encoding them (e.g., alcohol precipitate, frozen TE solution, lyophilizate and the like of a nucleic acid; lyophilizate of a protein, a fronzen liquid dissolved in a suitable buffer, and the like), and the above-mentioned vector, cells, reagent and culture medium for introduction of said factor. This kit may further contain a protocol or instructions describing the step of differentiation induction.

<Screening Method for Therapeutic or Prophylactic Agent for Treatment of Skeletal Muscle Disease>

The present invention provides a screening method of a candidate medicament, which is a medicament useful for the treatment or prophylaxis of a skeletal muscle disease.

In the present invention, a method of screening for an agent for the treatment or prophylaxis of a skeletal muscle disease can include the following steps:

(1) a step of contacting a candidate substance with a skeletal muscle cell differentiation-induced from an iPS cell derived from patient suffering from a skeletal muscle disease, (2) a step of selecting the substance as a therapeutic or prophylactic agent for skeletal muscle disease, when pathology of said skeletal muscle cell is mitigated as compared to no contact with the candidate substance.

In the present invention, the skeletal muscle disease may be myopathy. For example myopathy is muscular dystrophy, distal myopathies (e.g. Miyoshi myopathy), and so on. Muscular dystrophy is a pathology associated with deficiency or mutation of a dystrophin protein. Miyoshi myopathy is a pathology associated with mutated Dysferlin.

When the skeletal muscle disease is muscular dystrophy, the pathology of skeletal muscle cell can be observed as a deficiency or mutation of a dystrophin protein in said skeletal muscle cell or positive inflammation marker. Here, the inflammation marker may be, for example, the activity of prostaglandin D2 or NFkB. The mitigation of pathology can be confirmed, for example, by the expression of a dystrophin protein or a short dystrophin protein due to exon skipping, or a decrease of inflammation marker.

When the skeletal muscle disease is Miyoshi myopathy, the pathology of skeletal muscle cell can be observed as defective muscle membrane repair in said skeletal muscle cell. Here, the defective muscle membrane repair can be observed by uptake of FM1-43 in all cytoplasmic lesion. The mitigation of pathology can be confirmed, for example, by the decrease of the uptake of FM1-43.

In the present invention, examples of the candidate substance include a cell extract, a cell culture supernatant, a microorganism fermentation product, an extract derived from a marine organism, a plant extract, a purified protein or a crude protein, a peptide, a non-peptidic compound, a synthetic low-molecular-weight compound, and a natural compound.

In the present invention, the candidate substance can also be obtained by using any of many approaches in combinatorial library method known in the pertinent field including (1) a biological library, (2) a synthesis library method using deconvolution, (3) the "one-bead one-compound" library method, and (4) a synthesis library method using affinity chromatography selection. While the biological library method using affinity chromatography selection is limited to the peptide library, the other 4 approaches are applicable to peptide, nonpeptide oligomer, or low-molecular-weight compound library of compounds (Lam (1997) Anticancer Drug Des. 12: 145-67). An exemplary synthesis method of a molecule library can be found in the pertinent field (DeWitt et al. (1993) Proc. Natl. Acad. Sci. USA 90: 6909-13; Erb et al. (1994) Proc. Natl. Acad. Sci. USA 91: 11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). The compound library can be produced as a solution (see Houghten (1992) Bio/Techniques 13: 412-21) or beads (Lam (1991) Nature 354: 82-4), chips (Fodor (1993) Nature 364: 555-6), bacteria (U.S. Pat. No. 5,223,409), spores (U.S. Pat. Nos. 5,571,698, 5,403,484, and 5,223,409), plasmids (Cull et al. (1992) Proc. Natl. Acad. Sci. USA 89: 1865-9) or phage (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US application No. 2002103360).

EXAMPLES

<Method>
Cell Culture

Maintenance culture of human iPS cell lines (201B7, 253G1 and 253G4) was performed in the same manner as in the method of Takahashi et al. (K. Takahashi et al., Cell 131, 861, 2007). That is, human iPS cell was maintained using feeder cells. The feeder cells were produced by seeding 1,000,000 SNL per 10 cm tissue culture dish. As the maintenance medium, used was DMEM Glutamax F12 (Invitrogen, 500 ml) added with 2 mM L-Glutamine (NACALAI TESQUE), 1×Non-essential amino acid (Invitrogen), 50 mU/L Penicillin/50 µg/L Streptomycin (Invitrogen) and 100 µM 2-Mercaptoethanol (2-ME; NACALAI TESQUE) as the basal medium, which was added with Knockout Serum Replacement (KSR; Invitrogen) to 20% and 4 ng/ml bFGF (Wako). Human iPS cell after Tet vector introduction was maintenance-cultured in a medium further added with 100 µg/ml neomycin (NACALAI TESQUE).

Passage was performed when the colony of human iPS cell was 80-90% confluent. The feeder cells were removed with a cell dissociation solution [0.25% Trypsin (Invitrogen)/100 µg/ml collagenase IV (Invitrogen)/1 mM $CaCl_2$ (NACALAI TESQUE)/20% KSR], and thereafter scraped with a cell scraper. When dozens of cells became one mass, the whole was diluted about 3-fold, seeded on the next feeder cells, and cultured in an incubator at 37° C., 5% $CO_2$ in 100% humidity environment.

An immortalized human myoblast cell line Hu5/E18 provided by the RIKEN BRC was maintained and differentiated as described by Hashimoto (Hashimoto, N., et al. Mechanisms of development 125, 257-269, 2008).

Generation of an iPS Cell Line Derived from Miyoshi Myopathy (MM) Patient

Examples were approved by the authors' Institutional Review Board and conducted under the Declaration of Helsinki. A MM patient was encoded to protect their confidentiality, and written informed consent obtained. The MM patients were known to have two mutations in Dysferlin gene. The patient-derived iPS cells were generated from fibroblasts as described by Fusaki et al (Fusaki, N. et al., Proc Jpn Acad Ser B Phys Biol Sci 85, 348-362, 2009).

cDNA Cloning

As for MyoD, cDNA was purchased from MGC clone (MGC: 71135, GenBank: BC064493.1). The cDNA was amplified by PCR reaction using the following primers to give a cDNA fragment. As for Myf5, cDNA of differentiated human iPS cell was amplified by PCR reaction using KOD plus Neo as an enzyme to give a cDNA fragment. These cDNA fragments were incorporated into an entry vector as instructed in the package insert and using pENTR Directional TOPO Cloning Kits (Invitrogen). To be specific, PCR product (4 ng), Salt Solution (1 µl), distilled water (3.5 µl) and TOPO vector pENTR/D (1 µl) were reacted. Thereafter, the vector was incorporated into *Escherichia coli*, and the *Escherichia coli* was amplified to give an entry vector. The sequences of the primers used are as follows.

```
MyoD-Cloning Fw:
                                   (SEQ ID NO: 5)
CACCATGGAGCTACTGTCGCCA MyoD-Cloning Rv:
                                   (SEQ ID NO: 6)
TCAGAGCACCTGGTATATCGGGT Myf5-Cloning Fw:
                                   (SEQ ID NO: 7)
CACCATGGACGTGATGGATGGCTG Myf5-Cloning Rv:
                                   (SEQ ID NO: 8)
TCATAGCACATGATAGATAA
```

Production of Tetracycline Responsive Gene Forced Expression Vector

Figure 14:
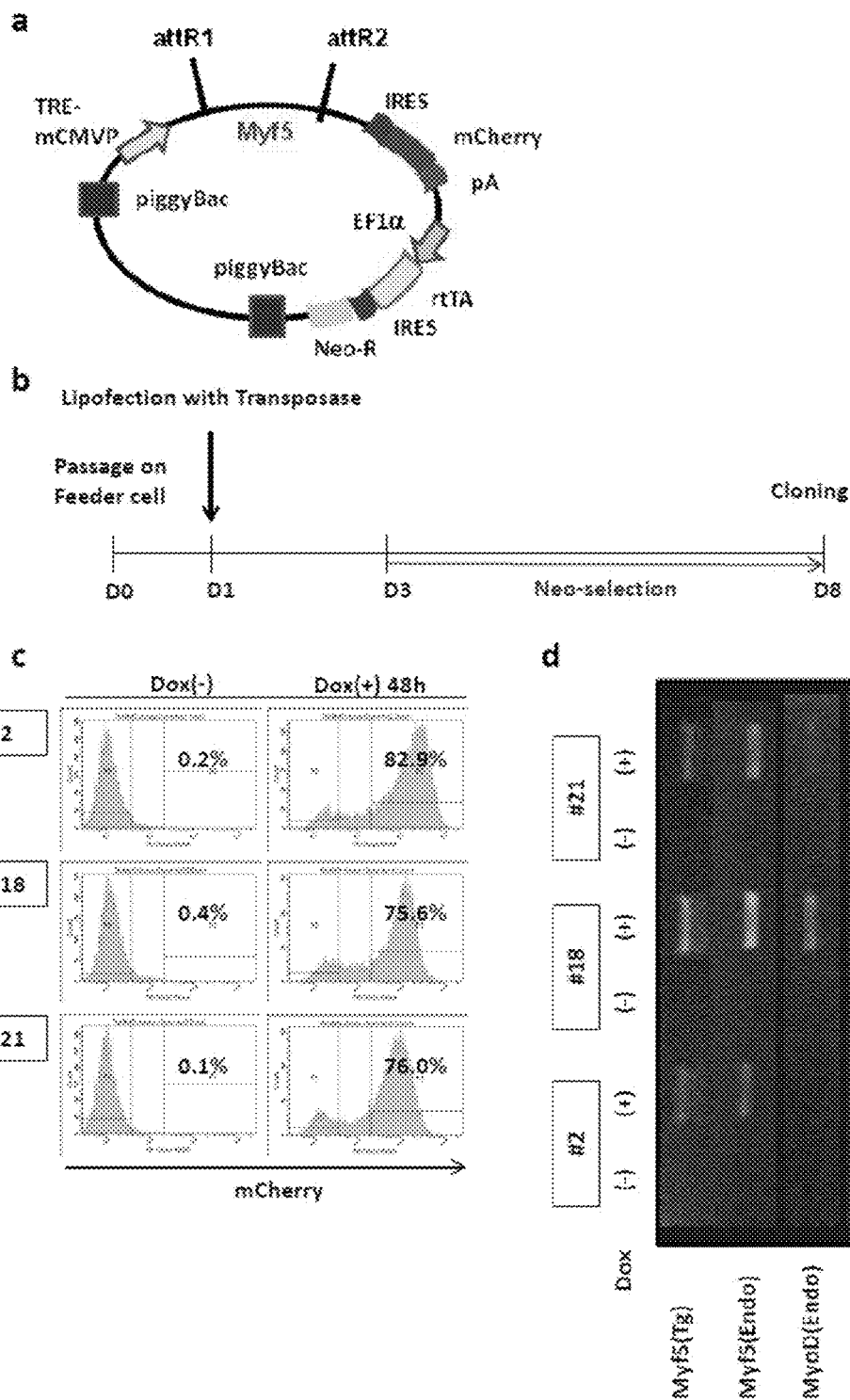
FIG. 14a shows the structure of a tetracycline responsive Myf5 expression piggyBac vector.
FIG. 14b shows the transformation protocol of iPS cell. In the Figure, D1 means day 1 after passage culture. On D1, transposase expression vector and tetracycline responsive Myf5 expression piggy-Bac vector were introduced into the cell by lipofection. On D8, cloning was performed.
FIG. 14c shows the results of the measurement of the expression intensity of mCherry by flow cytometer at 48 hr after Dox addition (Dox(+) 48 h) or non-addition (Dox(−)) in respective iPS cell lines (#2, #18 and #21) introduced with a tetracycline responsive Myf5 expression piggyBac vector.
FIG. 14d shows the expression levels of exogeneous Myf5 (Myf5(Tg)), endogenous Myf5 (Myf5(Endo)), endogenous MyoD (MyoD(Endo)) and Myogenin in the respective cell lines at 48 hr after Dox addition, which results were confirmed by PCR.

As a Tetracycline responsive gene forced expression piggyBac vector, KW111 developed by Woltjen et al. was used (K. Woltjen et al., Nature 458, 766, 2009). This vector incorporates both reverse tetracycline transactivator (rtTA) and tetracycline responsive region (TRE), and is designed to allow expression of mCherry in entrainment with the target gene (FIGS. 1a and 14a). In addition, selection by a drug is possible due to the neomycin resistance gene. This vector was mixed with an entry vector obtained by incorporating cDNA of MyoD or Myf5 in pENTR/D-TOPO, and tetracycline responsive MyoD (or Myf5) forced expression piggyBac vector Tet-MyoD (FIG. 1a) or Tet-Myf5 (FIG. 14a) was produced by a recombinant reaction using LR clonase (Invitrogen).

Introduction of Tet-Vector into iPS Cell

Human iPS cell lines in the number for a 10 cm dish were prepared. The previous day, the cells were cultured at a density of 3.3×10⁵ cells/well on a 6-well plate (IWAKI) gelatin coated with SNL feeder cells. Human iPS cell lines recovered in the same manner as in the maintenance culture were seeded on the 6-well plate wherein the SNL feeder cells were confluent. The next day, the vector was transfected. Tet-vector and a vector incorporating Transposase at the downstream of CAG-promoter (CAG-PBase) (each 1 μg) were prepared and dissolved in 100 μl of Opti-MEM (Invitrogen). Thereto was added 3-8 μl FugeneHD (Roche), and the mixture was blended in a Vortex for 2 sec. After reaction at room temperature for 15 min, the mixture was added to the culture medium in the 6-well plate, and cultured at 37° C. After 24 hr, the medium was changed, and 24 hr later, was further changed to a medium containing 100 μg/ml neomycin (NACALAI TESQUE). Thereafter, the medium was changed every day to a neomycin-containing medium, and the cells transformed to be neomycin resistant were selected.

Selection of Clone of Tet-MyoD and Tet-Myf5 iPS Cells

The obtained clone was seeded on a 6-well plate coated with Matrigel (Invitrogen) diluted 50-fold with the medium. From the next day, Doxycycline (Dox; LKT Laboratories) was added to a concentration of 1 μg/ml to the medium. The cells were recovered at 48 hr from Dox addition, the expression intensity of mCherry was analyzed by LSR Fortessa (BD) and clones showing high expression (FIGS. 3a, 5a, 12a and 14c) were selected.

Overexpression of Dysferlin in MM Patient-Derived iPSCs

The Dysferlin cDNA was inserted to a destination piggyBac (PB) vector which drives a gene of interest by EF1α promoter with co-expression of Puromycin resistant gene (PB-Dysferlin vector). Tet-MyoD transfected MM hiPSCs (MyoD-MM hiPSCs) were seeded onto mitomycin C-treated SNL-PH feeder cells which are resistant to Neomycin, Puromycin and Hygromycin. Next day, both 1 μg PB-Dysferlin vector and 1 μg PB transposase plasmid16 were transfected to MyoD-MM hiPSCs by FuGENE HD (Roche), according to manufacturer's protocol. After 48 hours of transfection, 100 μg/mL G418 (NACALAI TESQUE) and 1 μg/mL Puromycin (NACALAI TESQUE) were added for selection of the cell carrying both Tet-MyoD vector and PB-Dysferlin vector. After selection, appropriate MyoD-MM+Dysferlin hiPSC clones with proper Dysferlin expression were selected by Western Blotting.

Confirmation of MyoD Expression by Immunofluorescence Staining

The cells forced to express MyoD by the addition of Dox were fixed using 4% paraformaldehyde (NACALAI TESQUE)/PBS at room temperature for 20 min, washed three times with PBS for 5 min each time, and blocked with PBS added with 1% goat serum (Sigma), 0.1% bovine serum albumin (Sigma) and 0.2% Triton X-100 (NACALAI TESQUE) at room temperature for 1 hr. As the primary antibody, anti-MyoD (Rabbit Polyclonal; Santacruz) diluted at a concentration of 1:400 was added to the above-mentioned blocking solution. The antibody was reacted at 4° C. for 16-18 hr, and washed 3 times with 0.2% Triton X-100-added PBS (PBST). As the secondary antibody, anti-Rat IgG-Alexa488 (Molecular Probes) was diluted with PBST at 1:500, and reacted at 4° C. for 16-18 hr. Thereafter, to stain the cell nucleus, the cells were reacted with 5 μg/ml DAPI (Sigma) diluted 5000-fold with PBST at room temperature for 5 min, washed 3 times with PBS, and observed with an inverted fluorescence microscope system (KEYENCE).

Figure 7:
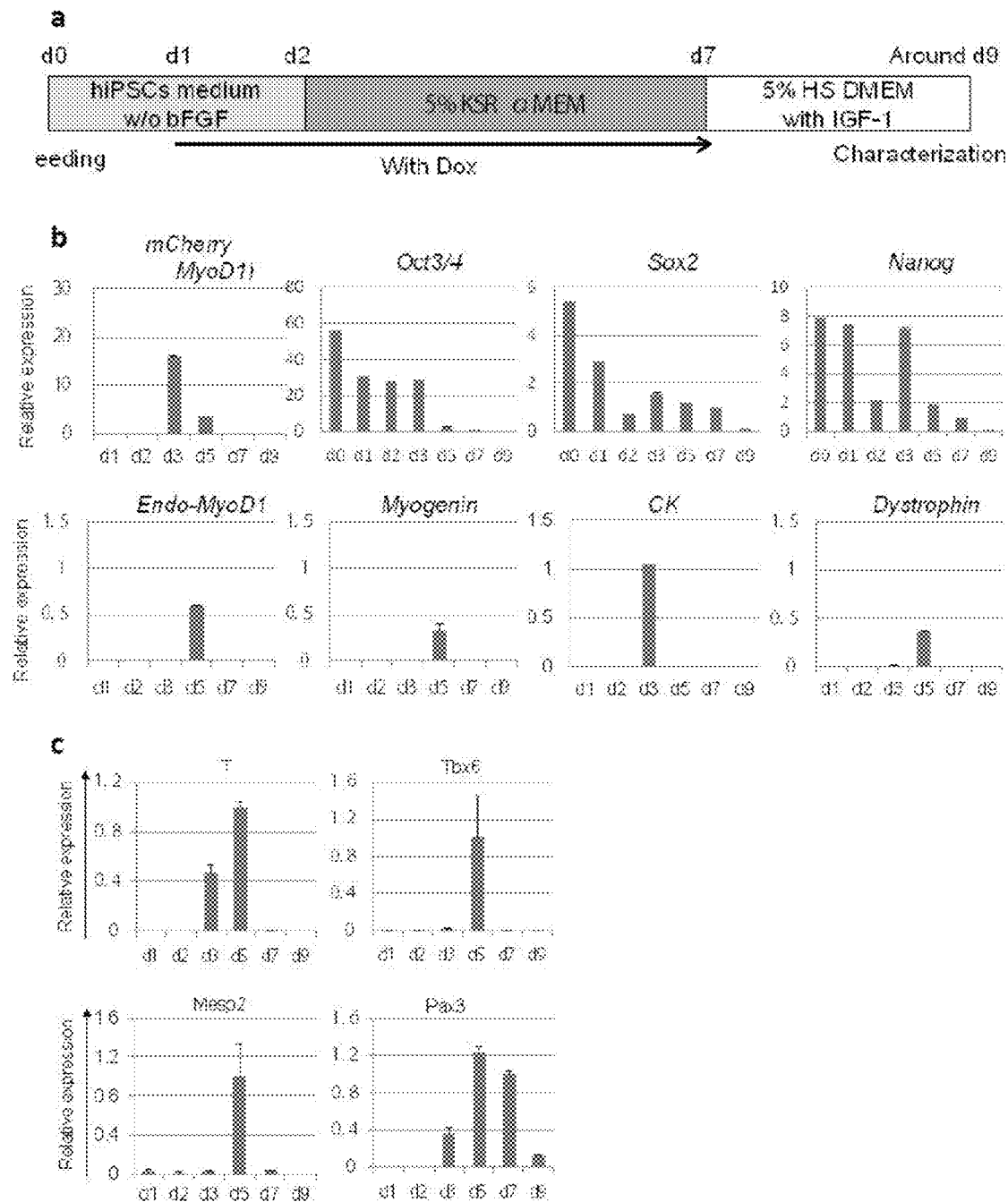
FIG. 7a shows the scheme of defined protocol for muscle differentiation of MyoD-hiPSCs.
FIG. 7b is a graph showing the relative expression of undifferentiated and myogenic marker genes in B7 #9 MyoD-hiPSC clone (n=3). Data are listed as mean±SD.
FIG. 7c is a graph showing the relative expression of premyogenic mesodermal marker genes in B7 #9 MyoD-hiPSC clone (n=3). Data are shown as the mean±SD.

Gene Expression Analysis by PCR mRNA was extracted from the cells with Sepasol®-RNA I Super G (NACALAI TESQUE), and cDNA was synthesized using a SuperScriptIII reverse transcription kit (Invitrogen) according to the protocol. The product thereof was subjected to conventional PCR reaction using the following primers and Ex Taq (TAKARA BIO), and a band of gene expression was confirmed by agarose gel electrophoresis. The PCR reaction was performed in a thermal cycler Veriti (ABI), and 25-30 cycles of reaction were performed at an annealing temperature of 60° C. Quantitative PCR was performed using probe sets, SYBR Green (Applied Biosystems), and Step One thermal cycler (Applied Biosystems). β-actin was used as the invariant controls. For standardization, the value of d7 sample was used as a control value (=1.0) (FIGS. 7b and c).

```
primers for conventional RT-PCR
Transgenic-MyoD (Tg) Fw:
                                      (SEQ ID NO: 9)
CACCATGGAGCTACTGTCGCCA Transgenic-MyoD (Tg) Rv:
                                     (SEQ ID NO: 10)
TCAGAGCACCTGGTATATCGGGT Endogenous-MyoD (Endo) Fw:
                                     (SEQ ID NO: 11)
GACTGCCAGCACTTTGCTATCT Endogenous-MyoD (Endo) Rv:
                                     (SEQ ID NO: 12)
CCTCAGAGCACCTGGTATATCG Transgenic-Myf5 (Tg) Fw:
                                     (SEQ ID NO: 13)
CACCATGGACGTGATGGATGGCTG Transgenic-Myf5 (Tg) Rv:
                                     (SEQ ID NO: 14)
TCATAGCACATGATAGATAA Endogenous-Myf5 (Endo) Fw:
                                     (SEQ ID NO: 15)
GCCTGAAGAAGGTCAACCAG Endogenous-Myf5 (Endo) Rv:
                                     (SEQ ID NO: 16)
ATTAGGCCCTCCTGGAAGAA Myogenin Fw:
                                     (SEQ ID NO: 17)
TGGGCGTGTAAGGTGTGTAA Myogenin Rv:
                                     (SEQ ID NO: 18)
CATGGTTTCATCTGGGAAGG CK-M Fw:
                                     (SEQ ID NO: 21)
GCATCTGGCACAATGACAAC CK-M Rv:
                                     (SEQ ID NO: 22)
CACCAGCTGCACCTGTTCTA Dystrophin Fw:
                                     (SEQ ID NO: 23)
AACAAAGCTCAGGTCGGATT Dystrophin Rv:
                                     (SEQ ID NO: 24)
ACTGGCATCTGTTTTTGAGG Oct3/4 Fw:
                                     (SEQ ID NO: 25)
GACAGGGGGAGGGGAGGAGCTAGG Oct3/4 Rv:
                                     (SEQ ID NO: 26)
CTTCCCTCCAACCAGTTGCCCCAAAC
```

-continued

Nanog Fw:
CAGCCCCGATTCTTCCACCAGTCCC (SEQ ID NO: 27)

Nanog Rv:
CGGAAGATTCCCAGTCGGGTTCACC (SEQ ID NO: 28)

Sox2 Fw:
GGGAAATGGGAGGGGTGCAAAAGAGG (SEQ ID NO: 29)

Sox2 Rv:
TTGCGTGAGTGTGGATGGGATTGGTG (SEQ ID NO: 30)

SeV Fw:
GGATCACTAGGTGATATCGAGC (SEQ ID NO: 31)

SeV Rv:
ACCAGACAAGAGTTTAAGAGATATGTATC (SEQ ID NO: 32)

β-actin Fw:
CTCTTCCAGCCTTCCTTCCT (SEQ ID NO: 19)

β-actin Rv:
CACCTTCACCGTTCCAGTTT (SEQ ID NO: 20)

Primers for Quantitative real-time RT-PCR
mCherry Fw:
CATCCCCGACTACTTGAAGC (SEQ ID NO: 33)

mCherry Rv:
CCCATGGTCTTCTTCTGCAT (SEQ ID NO: 34)

Endogenous-MyoD (Endo) Fw:
CACTCCGGTCCCAAATGTAG (SEQ ID NO: 35)

Endogenous-MyoD (Endo) Rv:
TTCCCTGTAGCACCACACAC (SEQ ID NO: 36)

CK-M Fw:
ACATGGCCAAGGTACTGACC (SEQ ID NO: 37)

CK-M Rv:
TGATGGGGTCAAAGAGTTCC (SEQ ID NO: 38)

Dystrophin Fw:
GATGCACGAATGGATGACAC (SEQ ID NO: 39)

Dystrophin Rv:
TGTGCTACAGGTGGAGCTTG (SEQ ID NO: 40)

β-actin Fw:
CACCATTGGCAATGAGCGGTTC (SEQ ID NO: 41)

β-actin Rv:
AGGTCTTTGCGGATGTCCACGT (SEQ ID NO: 42)

Differentiation Induction of Tet-MyoD iPS Cell into Skeletal Muscle Cell

Figure 2:
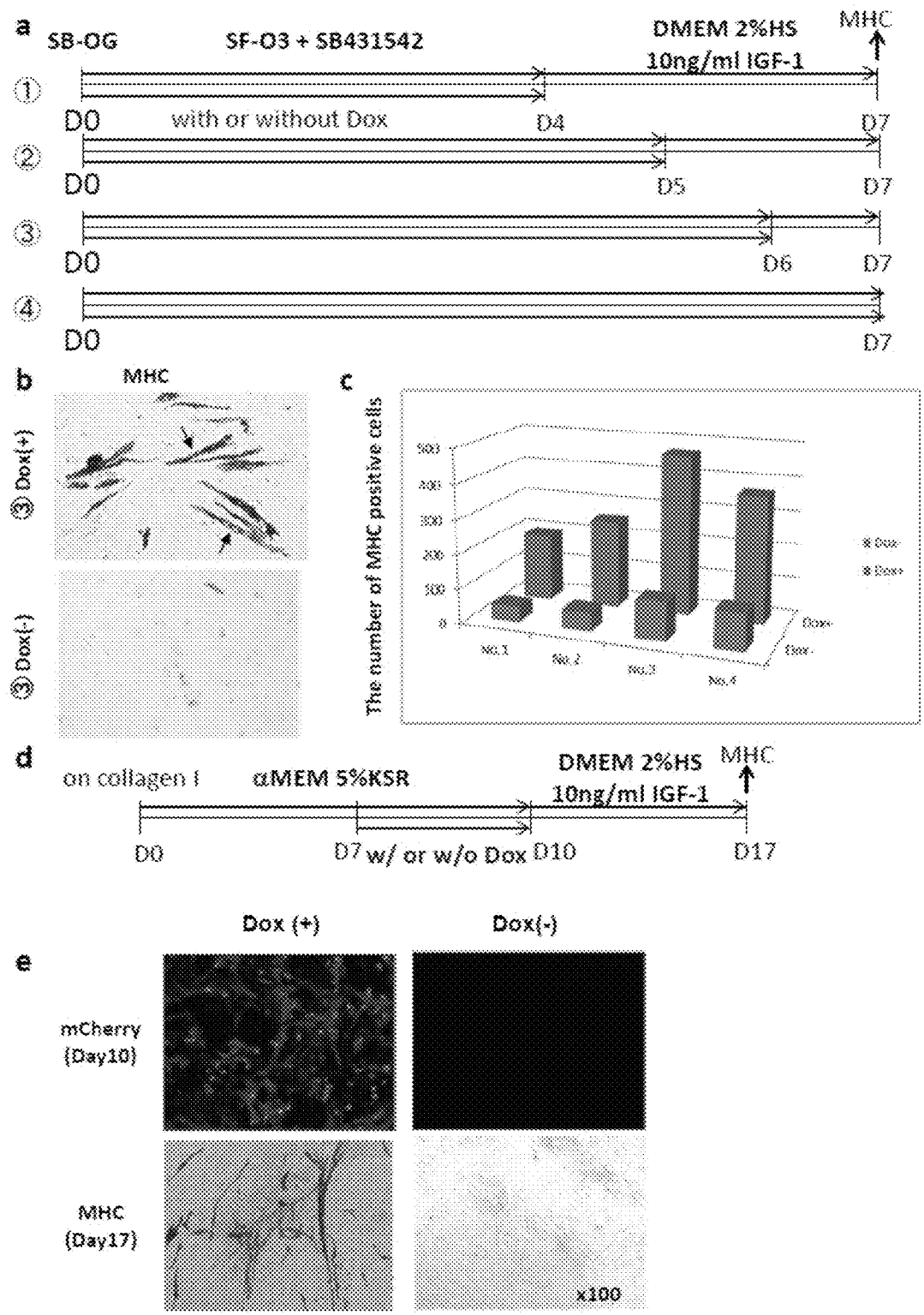

First, differentiation of skeletal muscle was induced using uncloned Tet-MyoD human iPS cells (FIG. 2a). According to the skeletal muscle progenitor cell induction method of Mahmood et al. (A. Mahmood, et al., J Bone Miner Res 25, 1216, 2010), the cells were induced to SB outgrowth cells, and thereafter, Dox was added to an SB outgrowth medium for 4 days. The SB outgrowth medium was a medium added with SF-03 (Sanko Junyaku), 0.2% bovine serum albumin (Sigma), 0.1% lipid (Invitrogen), 100 μM 2-ME, and 1 μM SB431542 (Milteny Bio). After the lapse of 4 days, the medium was changed to DMEM (NACALAI TESQUE) added with 2% horse serum (Sigma), IGF-1 (Peprotech, 10 ng/ml) and 100 μM 2-ME (2% Horse Serum DMEM). After the lapse of 4 days from the change of the medium, immunostaining was performed to confirm differentiation induction into skeletal muscle.

As second differentiation induction method (FIG. 2d), the paraxial mesoderm induction method by Sakurai et al. was performed after partial alteration. Specifically, the cells were seeded on a Collagen I coat dish (IWAKI) for passage, and the medium was changed to αMEM (NACALAI TESQUE) added with 5% KSR and 100 μM 2-ME. Doxycycline (Dox) was added thereto from Day 7 after the seeding, and the medium was changed on Day 10 to the same 2% Horse Serum DMEM medium as in the above-mentioned induction method. Addition of Dox was continued here. On Day 17, immunostaining was performed to confirm differentiation induction into skeletal muscle.

Figure 4:
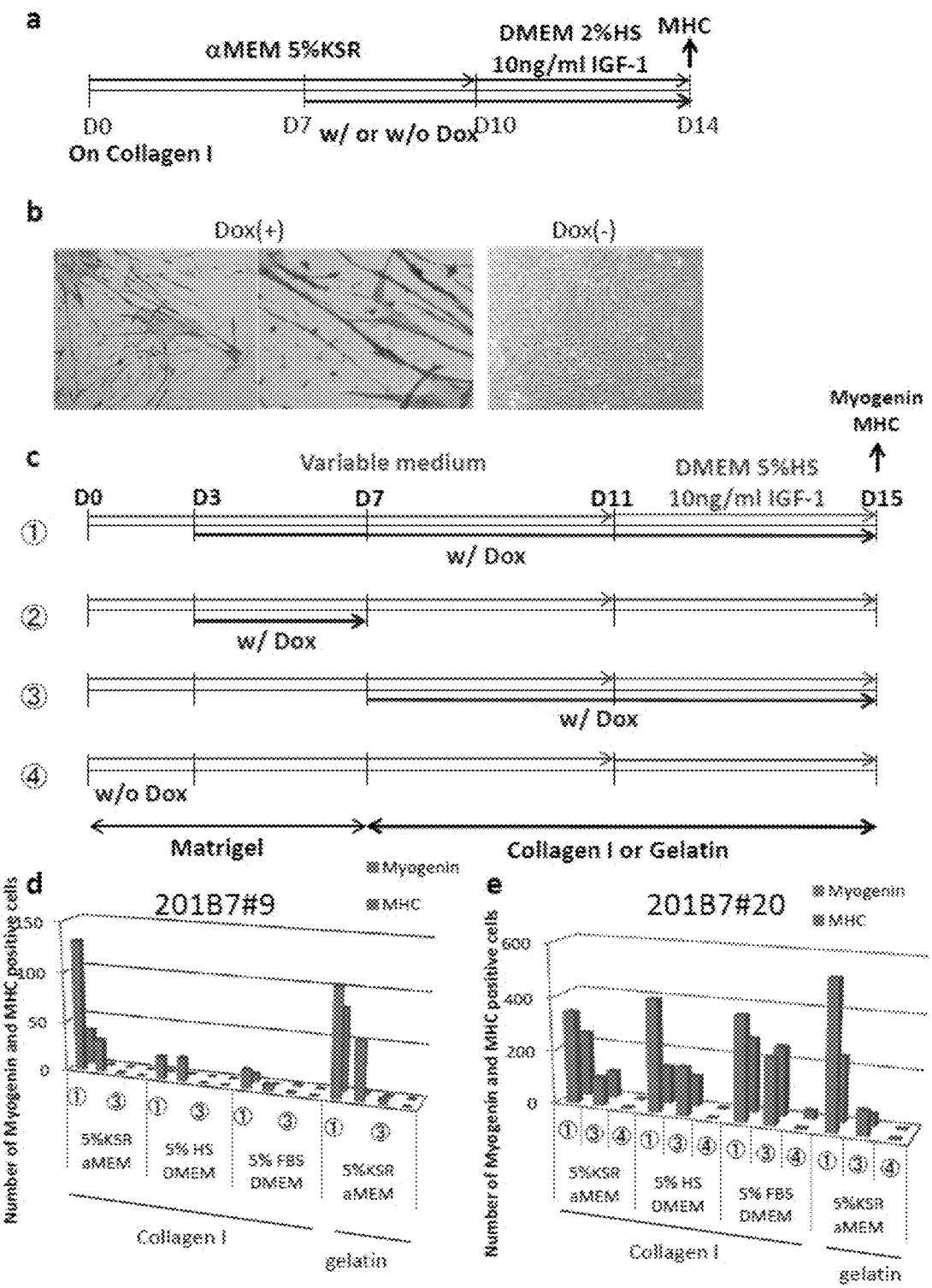
FIG. 4a shows the protocol of the skeletal muscle cell induction from a cloned human iPS cell, which uses a paraxial mesoderm induction method and MyoD induction expression in combination.
FIG. 4b shows stained images with an anti-MHC antibody of the cells of addition group (Dox(+)) and non-addition group (Dox(−)), when differentiation of clone #16 was induced.
FIG. 4c shows the protocol for the consideration of the timing of Dox addition for the skeletal muscle cell induction. In the Figure, ① means that the cells were cultured with Dox addition from days 3 to 15 after the start of the differentiation induction, ② means that the cells were cultured with Dox addition from days 3 to 7, ③ means that the cells were cultured with Dox addition from days 7 to 15, and means that the cells were cultured without Dox addition.
FIG. 4d is a graph showing the Myogenin and MHC positive cell numbers under the respective culture conditions for clone B7 #9.
FIG. 4e is a graph showing the Myogenin and MHC positive cell numbers under the respective culture conditions for clone B7 #20.
Figure 6:
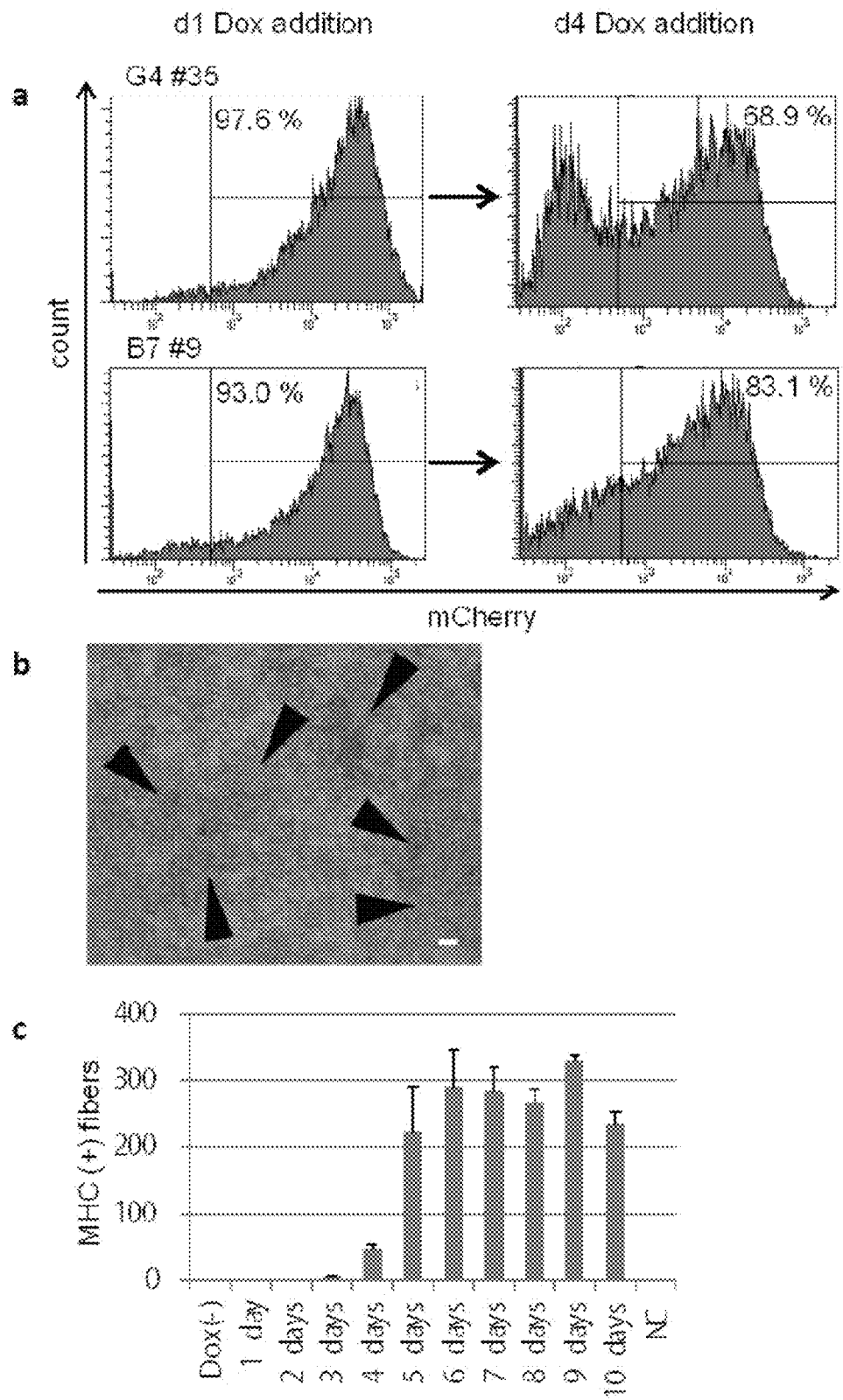
FIG. 6a shows the results of Flow cytometric analysis of MyoD-hiPSCs with 24 hour (d1) Dox treatment in different start points. Dox addition at differentiation day 1 promoted higher percentage of mCherry expression in MyoD-hiPSCs than Dox addition at differentiation day 4.
FIG. 6b shows the merged image of phase-contrast and mCherry images in differentiated MyoD-hiPSCs which were administrated Dox at differentiation day 4. No mCherry expression area (arrowheads) indicates Dox-unresponsive MyoD-hiPSCs.
FIG. 6c shows the graph of MHC positive myogenic cell number derived from MyoD-hiPSCs during 11 days differentiation with various administration periods of Dox.

As third differentiation induction method, appropriate conditions were examined by variously changing the coating of a culture dish, medium and the term of addition of Dox. The coating substrates used were Collagen I, Matrigel (Invitrogen) and 0.1% Gelatin (NACALAI TESQUE). The media used were 3 kinds of (1) αMEM added with 5% KSR and 100 μM 2-ME (5% KSR αMEM), (2) DMEM (NACALAI TESQUE) added with 5% Horse Serum, IGF-1 10 ng/ml and 100 μM 2-ME (5% HS DMEM) and (3) DMEM added with 5% FBS, 100 μM 2-ME and 1% Ultroser G (PALL Life Sciences) (5% FBS DMEM) (FIG. 4c and FIG. 6). Under any conditions, a Matrigel Coat 10 cm dish was used for the initial 7 days, the cells were dissociated with 0.25% trypsin/1 mM EDTA at this time point, $1 \times 10^5$ cells were seeded per 1 well of a 24-well plate and the culture was continued.

As final differentiation induction method (FIG. 7), MyoD-hiPSCs were seeded onto collagen I coated dish (IWAKI) or Matrigel (BD) coated dish without feeder cells. Matrigel was diluted 1:50 with primate ES medium. MyoD-hiPSCs were trypsinized and dissociated into single cells. The number of cells for one well of a 6 well culture plate was ranged from $2.0 \times 10^5$ to $1.0 \times 10^6$. Culture medium was changed to human iPS medium without bFGF and with 10 μM Y-27632 (NACALAI TESQUE). After 24 hours, 1 μg/mL doxycycline (LKT Laboratories) was added to the culture medium. After additional 24 hours, culture medium was changed to alpha Minimal Essential Medium (αMEM) (NACALAI TESQUE) with 5% Knockout Serum Replacement (KSR) (Invitrogen), 50 mU/L Penicillin/50 μg/L Streptomycin (Invitrogen) and 100 μM 2-Mercaptoethanol (2-ME). After additional 5 days, culture medium was changed to DMEM with 5% horse serum (Sigma), 50 mU/L Penicillin/50 μg/L Streptomycin, 10 ng/mL Recombinant human insulin-like growth factor 1 (Peprotech), 2 mM L-Glutamine and 100 μM 2-ME. About 2 days later, myogenic products were assessed.

siRNA Transfection

The siRNA for T, Tbx6 and negative control were purchased (Sigma, SASI_Hs01_00221962, SASI_Hs01_00166068 and SIC-00110). Fifty nM of siRNA was transfected into hiPS cells seeded at a density from 2.0 to $3.0 \times 10^5$ cells in 6-well plates on day 0 and 3, respectively.

The siRNA was transfected using Lipofectamine RNAiMAX (Invitrogen) according to the manufacturer's protocol.

Differentiation Induction of Tet-Myf5 iPS Cell into Skeletal Muscle Cell

Tet-Myf5 iPS cell clone was prepared in the cell number for one 6 cm dish, and the cells were seeded on a 10 cm dish coated with Matrigel diluted 50-fold with the medium in the same manner as in the maintenance culture. The next day, Dox was added to the medium for human iPS cell, and the medium was changed every day until Day 7 after the seeding. On Day 7 after seeding, the cells were dissociated with 0.25% trypsin/1 mM EDTA, and seeded on a Type I collagen coat 24 well plate (IWAKI) at a density of $1\times10^5$ cells per well. The medium used was αMEM added with 100 μM 2-ME and 50 mU/L Penicillin/50 μg/L Streptomycin, and further added with 5% KSR. After culturing in this medium for 48 hr, the medium was changed to DMEM/F12 (Invitrogen) added with 2 mM L-glutamine (NACALAI TESQUE), 1×Non-essential amino acid (Invitrogen), 100 μM 2-ME, and 50 mU/L Penicillin/50 μg/L Streptomycin, and further added with 2% Horse Serum, and the cells were further cultured for 48 hr.

Immunostaining of Differentiated Skeletal Muscle

The differentiated cells were fixed with 2% paraformaldehyde (NACALAI TESQUE)/PBS at 4° C. for 10 min, washed 3 times with PBS for 5 min each time, and discolored with methanol (NACALAI TESQUE) added with 1% hydrogen peroxide (Wako) for 15 min. The mixture was washed 3 times again with PBS at 4° C. for 5 min and blocked with 2% skim milk (BD)/PBST (PBSMT) at 4° C. for 15 min. As the primary antibody, rat monoclonal antibody (mAb) Laminin (1:15; ALEXIS), mouse mAb Anti-human Myosin heavy chain (MF20) (1:400; R&D), mouse mAb myogenin (F5D) (1:400; SANTA CRUZ), rabbit polyclonal antibody (pAb) MyoD (M-318) (1:400; SANTA CRUZ), mouse mAb human Spectrin (1:100; Leica), mouse mAb anti-human nuclei (1:200; MILLIPORE), mouse mAb alpha skeletal muscle actin (1:200; Acris), rabbit pAb Creatine Kinase M (Y14) (1:100; Bioworld Technology) and mouse mAb anti Dysferlin (NCL-Hamlet) (1:25; Leica) were each diluted with the above-mentioned PBSMT blocking solution and used. The cells were reacted at room temperature for 1 hr, and washed 3 times with PBSMT. As the secondary antibody, Alexa fluor488 conjugated goat-anti-rabbit or mouse IgG, Alexa fluor568 conjugated goat-anti-rabbit or mouse IgG (all 1:500; all from Invitrogen), and HRP conjugated goat-anti-mouse IgG (1:200 in IHC and 1:2000 in Western blotting; Vector) diluted with PBSMT was added, and the mixture was reacted at room temperature for 1 hr. After washing twice with PBSMT at room temperature for 10 min, and once with PBST for 10 min, the color was developed with a DAB coloring kit (NACALAI TESQUE). After appropriate color development, the cells were washed with PBST to quench the reaction. Samples were observed with LMS710 confocal microscopy (Carl Zeiss) or an inverted microscope (OLYMPUS).

Transplantation Studies

Nonobese diabetic/severely combined immunodeficient (NOD/SCID) mice were purchased from Charles River Laboratories, and were mated with DMD-null mice which do not express Dystrophin. NOD-DMD mice were generated and used for in vivo transplantation studies. Before intramuscular cell transplantation, mice were injured with cardiotoxin, following diethyl ether anesthesia. At 24 hours after cardiotoxin damage, day 6 MyoD-hiPSCs ($1.0\times10^6$– $9.5\times10^6$ cells/50 ml 10% Matrigel in aMEM) were injected into left TA muscles. All mice used in this study were humanely sacrificed 28 days after transplantation and tissue samples were collected.

Co-Culture with C2C12 Cells

Differentiated MyoD-hiPSCs were co-cultured with GFP integrated C2C12 cell line. First, MyoD-hiPSCs were differentiated for 7 days. And on 7th day, medium was replaced to DMEM supplemented with 5% horse serum and $1.0\times10^5$ C2C12 cells were seeded onto MyoD-hiPSCs. Bio Station CT (Nikon) was used to time-lapse observation for co-cultured samples. Shoot duration was an hour.

Mitochondrial Staining

MitoTracker Red CMXRos (Invitrogen) was used according to provided protocol. Samples were observed with BZ-9000E (Keyence).

<Results>

Production and Evaluation of Tet-MyoD hiPSC

The aforementioned Tet-MyoD vector was transfected to human iPS cells, the cell groups that obtained neomycin resistance were divided into a Doxycyclin (Dox)-addition group and a Dox non-addition group, and the expression of mCherry and MyoD was observed 24 hr later. It was confirmed that MyoD protein was expressed in consonance with mCherry only in the Dox-addition group (FIG. 1c). In addition, in a similar experiment, expression analysis at an mRNA level was also performed. As a result, exogenous MyoD (Tg) was strongly induced in the Dox-addition group, and endogenous MyoD (Endo) was also induced (FIG. 1d). Since a weak expression of exogenous MyoD was also found in the Dox non-addition group, a cell that leaks expression even in a Dox-free condition is considered to be present, which suggests the necessity of the selection of the clones (FIG. 1d). Myosin heavy chain (MHC) positive or myogenin positive myofibers with multi-nuclei were detected 7 days after Dox administration (FIG. 1e).

Next, the differentiation ability of Tet-MyoD hiPSC was examined. First, it was verified by the SB-outgrowth (SB-OG) cell induction method (A. Mahmood, et al., J Bone Miner Res 25, 1216, 2010), which is a skeletal muscle cell induction method reported heretofore. As shown in FIG. 2a, the obtained SB-OG cells were differentiation-induced by changing the Dox-addition term and induction term in 2% Horse serum DMEM ("DMEM 2% HS 10 ng/ml IGF-1" in the Figure) medium, and Myosin Heavy Chain (MHC) positive cell number was measured and evaluated. The representative images of the staining are shown in FIG. 2b. A number of MHC positive cells were found to have been stained brown in the Dox-addition group, with a part thereof having polynuclei, which suggests that they were matured skeletal muscle cells (FIG. 2b, arrow). On the other hand, tiny MHC positive cells were occasionally found in the Dox non-addition group (FIG. 2b, lower Figure). By the cell count, the Dox-addition group showed a 5- to 10-times greater number of MHC positive skeletal muscle cells under any conditions as compared to the non-addition group. In addition, by comparison between the Dox-addition groups, most efficient differentiation into MHC positive skeletal muscle cells was found with the addition of Dox for 6 days and culture in a 2% Horse serum DMEM medium for 1 day (FIG. 2c). In addition, differentiation into skeletal muscle was also found by a different differentiation induction method. As shown in FIG. 2d, undifferentiation hiPS cells were differentiated on a Collagen I dish for 7 days, divided into a Dox-addition group and a Dox non-addition group and further cultured for 3 days, after which the cells were differentiation-induced in a 2% Horse serum DMEM medium for 7 days, and the MHC expression was observed.

On Day 10 of the differentiation, expression of mCherry was found only in the Dox-addition group, and on Day 17 of the differentiation, MHC positive skeletal muscle cells were found only in the Dox-addition group (FIG. 2e). In consideration of the fact that this induction method showed no differentiation of MHC positive skeletal muscle cells in the Dox non-addition group, it was found that MyoD forced expression by tetracycline can sufficiently induce differentiation of skeletal muscle even under culture conditions that do not support skeletal muscle differentiation.

Clone Selection of Tet-MyoD hiPSC

Figure 3:
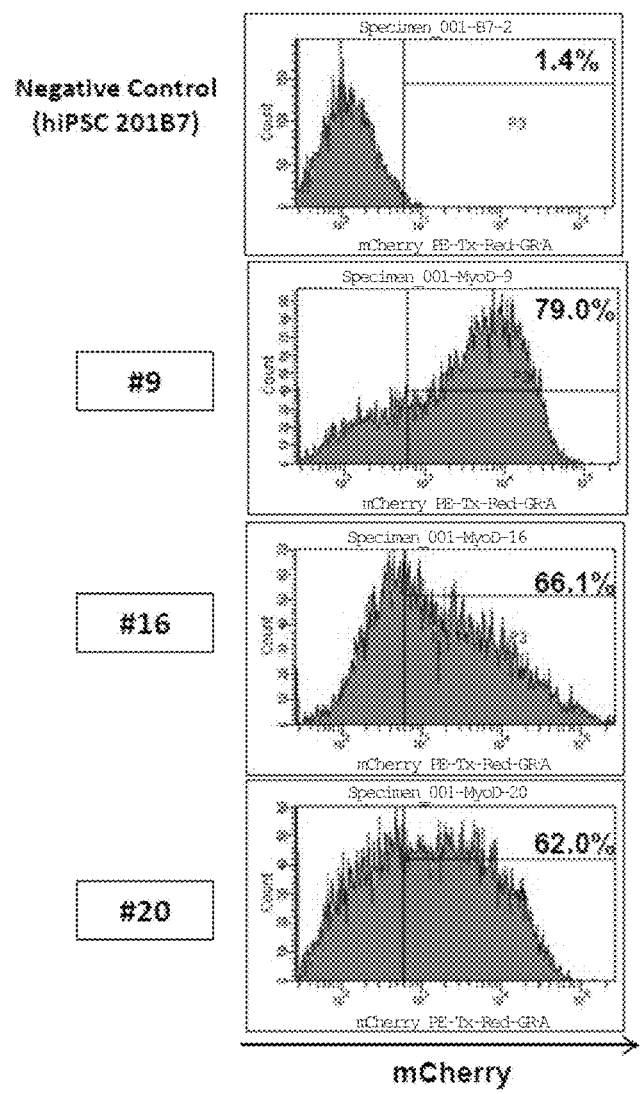
FIG. 3a shows the results of the measurement of the expression intensity of mCherry by flow cytometer after Dox addition in respective iPS cell lines (#9, #16 and #20) introduced with a tetracycline responsive MyoD expression piggyBac vector. In the Figure, the mCherry positive cell rates of respective cell lines are shown.
FIG. 3b shows the expression levels of exogeneous MyoD (MyoD(Tg)) and endogenous MyoD (MyoD(Endo)) in respective cell lines at 48 hr after Dox addition, which results were confirmed by PCR.
Figure 3:
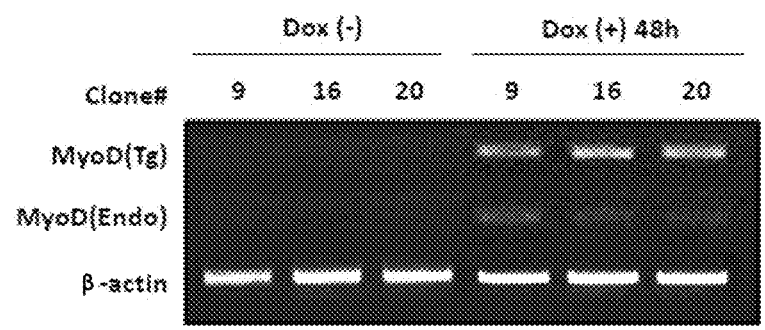

Clones were selected as mentioned above. The mCherry expression intensity was compared with Negative Control 201B7 free of genetic modification. Among 24 clones, Clone Nos. 9, 16 and 20 (B7 #9, B7 #16, B7 #20) were selected, which showed comparatively high mCherry expression (FIG. 3a). In addition, the clones were divided into a Dox-addition group and a non-addition group, mRNA was recovered 48 hr later, and the gene expression was analyzed by PCR (FIG. 3b). In the Dox non-addition group, expression with leakage for exogenous MyoD (Tg) was not found and expression of endogenous MyoD (Endo) was not found, either (FIG. 3b). In the Dox-addition group, expression of both MyoD (Tg) and MyoD (Endo) was found in all clones. It has been confirmed that Dox induces foreign gene expression and also expresses endogenous MyoD (FIG. 3b).

Skeletal Muscle Cell Induction from Tet-MyoD hiPSC Clone

First, using B7 #16, a skeletal muscle differentiation ability was qualitatively evaluated. The differentiation induction was performed as shown in FIG. 4a, and expression of MHC was observed 14 days later. In the Dox-addition group, a number of MHC positive skeletal muscle cells stained brown were confirmed (FIG. 4b, Left). By observation at a high magnification, skeletal muscle cells having polynuclei and considered to have been matured were also found (FIG. 4b, Center). In contrast, in the Dox non-addition group, MHC positive cell was not found at all (FIG. 4b, Right). Therefrom it was found that induction of differentiation into matured skeletal muscle cell by Dox was possible even in the selected Tet-MyoD clones.

Using B7 #9 and B7 #20, optimal conditions were examined by the measurement of MHC positive cells. As shown in FIG. 4c, the Dox addition term was changed, and further, the composition of the medium was changed, and 16 conditions were compared in B7 #9 (FIG. 4d) and 12 conditions were compared in #20 (FIG. 4e). In B7 #9, in the study of the Dox-addition term, addition of Dox in the term of Day 3-7 of differentiation was found to be important (FIG. 4d ① and ②). By comparison of the media, 5% KSR aMEM was most suitable, and coating of the culture dish showed no difference between Collagen I and Gelatin (FIG. 4d). B7 #20 was not influenced by the composition of the medium and the coating (FIG. 4e), and many MHC positive skeletal muscle cells were found with the long Dox-addition term (FIG. 4e ① and ③). From the above-mentioned results, it was found with Tet-MyoD hiPSC that mature skeletal muscle cells could be induced in about 2 weeks by adding Dox in a somewhat early differentiation stage from about Day 3 of differentiation induction, and thereafter continuously adding Dox for not less than 4 days.

Additional Clone Selection of Tet-MyoD hiPSC

Figure 5:
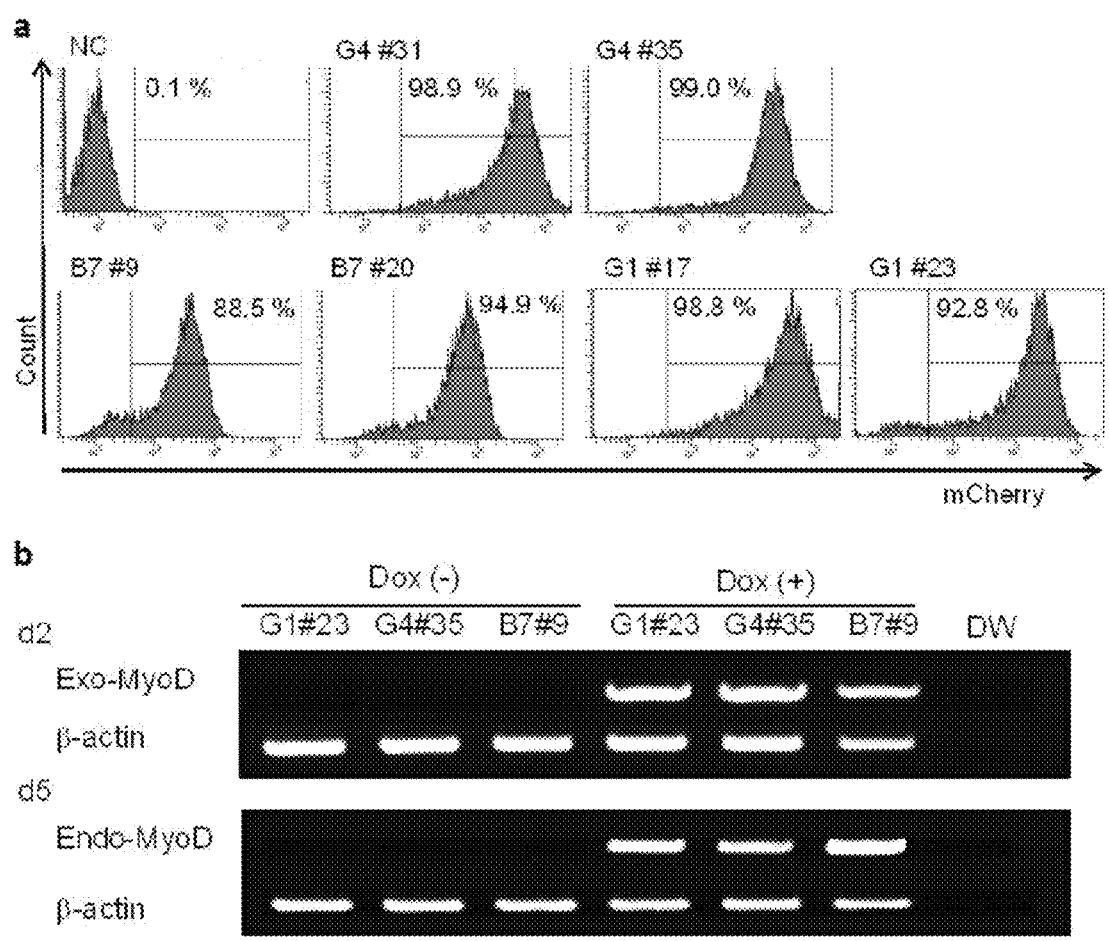
FIG. 5a shows the results of the measurement of the expression of mCherry which is synonymous with exogenous MyoD1 driven by Dox treatment for one day in parent iPS cell clone as negative control (NC) and each transfected human iPS cell clones (MyoD-hiPSC clones; G4#31, G4#35, B7#9, B7#20, G1#17, and G1#23).
FIG. 5b shows the result of RT-PCR analyses of each MyoD-hiPSC clone. Cloned MyoD-hiPSCs had no leaky expression of exogenous MyoD1 without Dox, while they could express exogenous MyoD1 24 hours (d2) after Dox addition. Endogenous MyoD1 could be promoted 96 hours (d5) after Dox addition.

Clone G4 #31, G1 #17 and G1 #23 were furthermore selected, which showed comparatively high mCherry expression (FIG. 5a). The expression of endogenous MyoD1 without leak of exogenous MyoD1 were confirmed among the MyoD-hiPSC clones derived from three distinct hiPS cell lines 201B7, 253G1 and 254G41 (FIG. 5b).

Protocol for Differentiation

First, it was determined that the start point of Dox administration at day 1 because of the high emergence of mCherry positive cells (FIG. 6a). Further differentiated MyoD-hiPSCs were unresponsive at day 4, even in the presence of Dox (FIG. 6b, arrowhead). Secondly, it was determined that the period of Dox administration more than 5 days, because they were enough to lead MyoD-hiPSCs committing to myogenic lineage (FIG. 6c). Finally, the protocol was established for myogenic differentiation of MyoD-hiPSCs (FIG. 7a).

According to the differentiation protocol (FIG. 7a), time course gene expression of both undifferentiated and myogenic markers were analyzed (FIG. 7f). The mCherry expression which was synonymous with exogenous MyoD1 expression was primarily detected at day 2. The expression of undifferentiated markers, such as Oct3/4, Sox2 and Nanog, gradually decreased through the course of differentiation (FIG. 7b). The expression of both endogenous MyoD1 and Myogenin, which are positively regulated by MyoD1, appeared at day 3 and reached their peak expression at day 7 (FIG. 7b). Furthermore, mature myofiber markers, such as creatine kinase muscle isoform (CK-M) and dystrophin, were also detected following exogenous MyoD1 expression (FIG. 7b). Such expression pattern indicates that the exogenous MyoD1 can also act as a dominant regulator for myogenesis in the same machinery as development even in premature cells.

To further assess whether Dox-induced myogenic differentiation proceeded via mesodermal differentiation, expression of mesodermal marker genes were analyzed. Unexpectedly, pan-mesodermal marker brachyury (T), paraxial mesodermal markers, such as Mesp2, and Tbx6, and Dermomyotome marker Pax3 were expressed transiently during differentiation (FIG. 7c).

Analysis for the Role of Mesodermal Gene Expression

Figure 8:
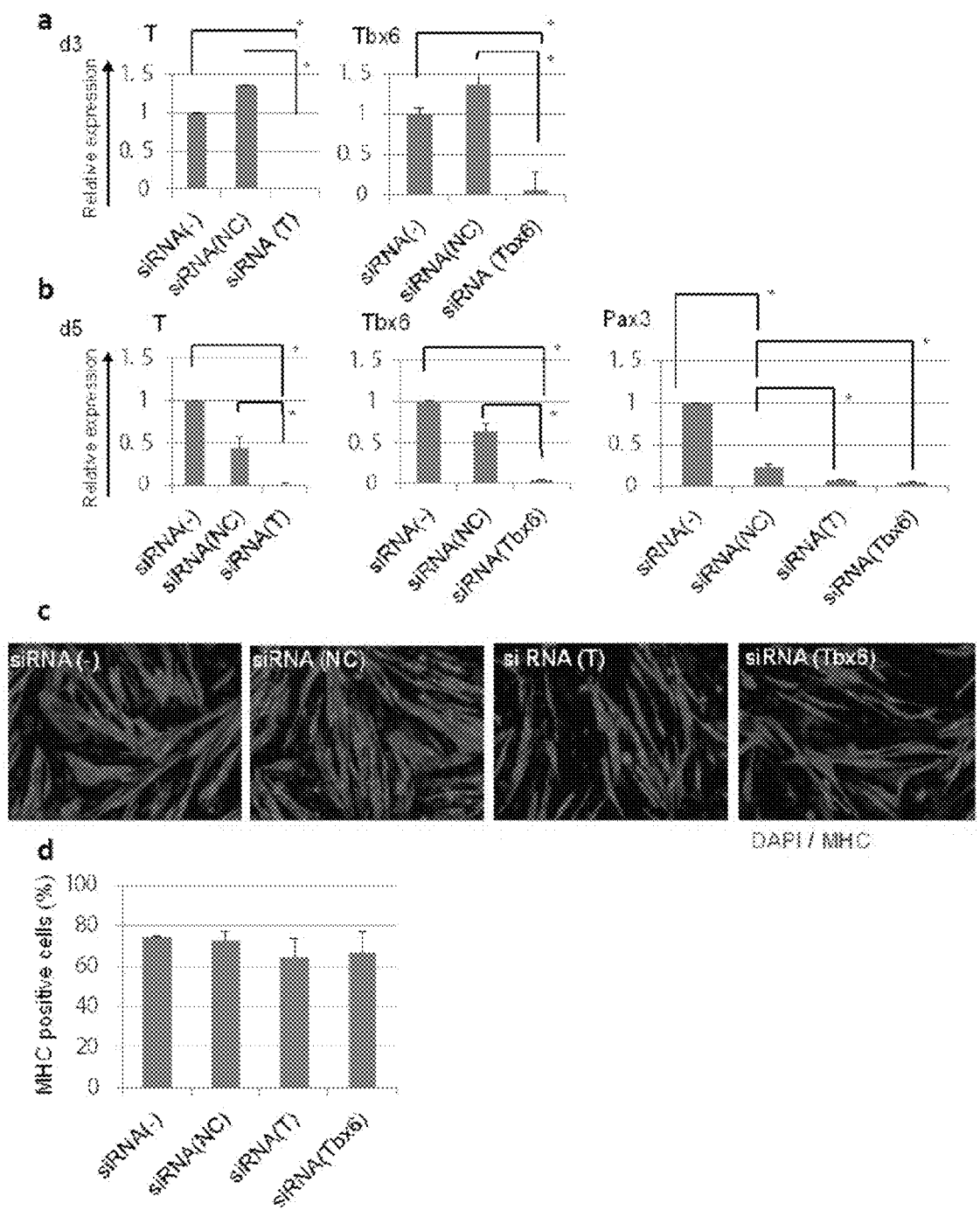
FIG. 8a is a graph showing the relative expression of T and Tbx6 in B7 #9 MyoD-hiPSC clone (n=3) on day 3 after suppression by siRNA. The siRNAs for T and Tbx6 were added twice on day 0 and day 3 to differentiation culture of MyoD-hiPSCs. *: p<0.05.
FIG. 8b is a graph showing the relative expression of T, Tbx6 and Pax3 in B7 #9 MyoD-hiPSC clone (n=3) on day 5 after suppression of T and Tbx6 by siRNA. The siRNAs for T and Tbx6 were added twice on day 0 and day 3 to differentiation culture of MyoD-hiPSCs. *: p<0.05.
FIG. 8c shows anti-MHC antibody-stained images of differentiated B7 #9 MyoD-hiPSCs with or without siRNA treatment.
FIG. 8d shows the graph of percentage of the MHC positive cells on 9 days after differentiation with or without siRNA treatment in B7 #9 MyoD-hiPSC clone (n=3).

To address whether such mesodermal gene expression is essential for myogenic differentiation in this protocol, mesodermal gene expression was suppressed with the siRNA for T or Tbx6 during early phase of differentiation. Expressions of T or Tbx6 were strongly suppressed on day 3 and 5 by the siRNA, respectively (FIGS. 8a and 8b). Furthermore, expression of Pax3, which is the upstream gene of MyoD1, was also suppressed by the siRNAs for both T and Tbx6. Despite suppressions of mesodermal gene expressions, the efficiencies of myogenic differentiation were not affected (FIGS. 8c and 8d). It was suggested that exogenous expression of MyoD1 in undifferentiated hiPSCs can promote premyogenic mesodermal genes expression in the cells, but a major population of undifferentiated hiPSCs directly differentiate into mature myocytes.

Clonal Variation

Figure 9:
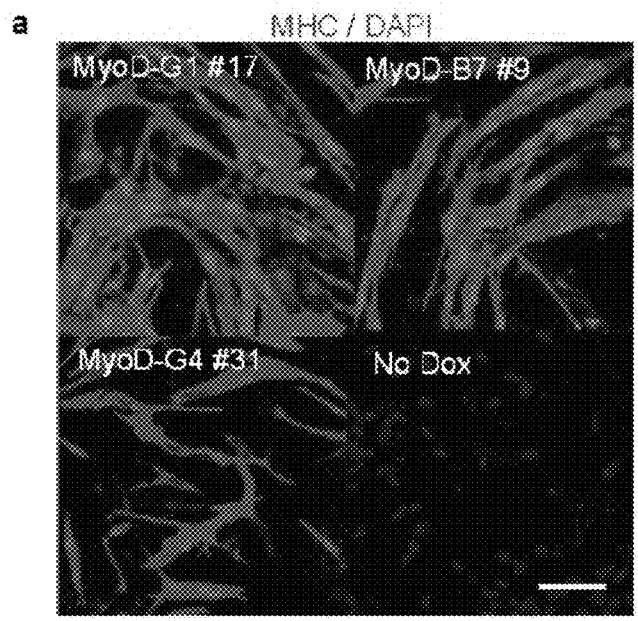
FIG. 9a shows anti-MHC antibody-stained images (red) of differentiated MyoD-hiPSCs or undifferentiated MyoD-hiPSCs. A scale bar shows 100 µm.
FIG. 9b shows the graph of percentage of MHC positive cells per total cells of MyoD-hiPSC clones. (n=3 in each clone). Data are listed as mean±S.D.
FIG. 9c shows the fluorescence microscope images of mitochondria in both undifferentiated and differentiated MyoD-hiPSCs. A scale bar shows 20 µm.
FIG. 9d shows image for immunohistochemistry of differentiated MyoD-hiPSCs for mature myogenic markers (skeletal muscle actin and CK-M). A scale bar shows 20 µm.
Figure 9:
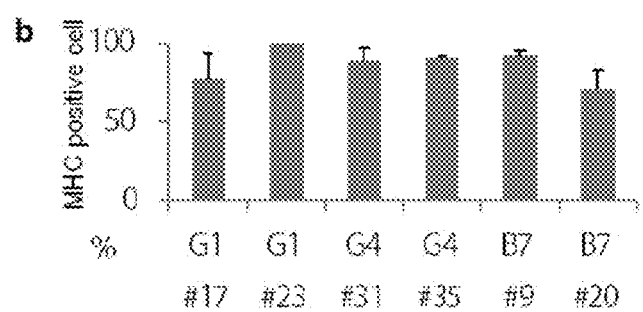
Figure 9:
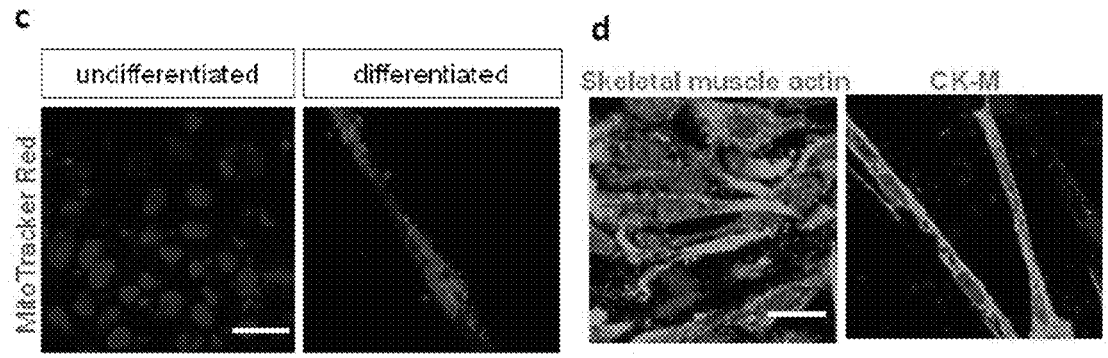

In this differentiation system, all three distinct hiPSC clones could be promoted into MHC positive myofibers (FIG. 9a), and the efficiency of MHC positive cells ranged from 70 to 90% without relation to original clones (FIG. 9b). Differentiated MyoD-hiPSCs changed their shape to spindle-like uniformly. Thus, this differentiation system overcomes clonal variation, and actualizes efficient and uniform myogenic differentiation by dominant expression of exogenous MyoD1.

Assessment of Myogenic Properties

Figure 10:
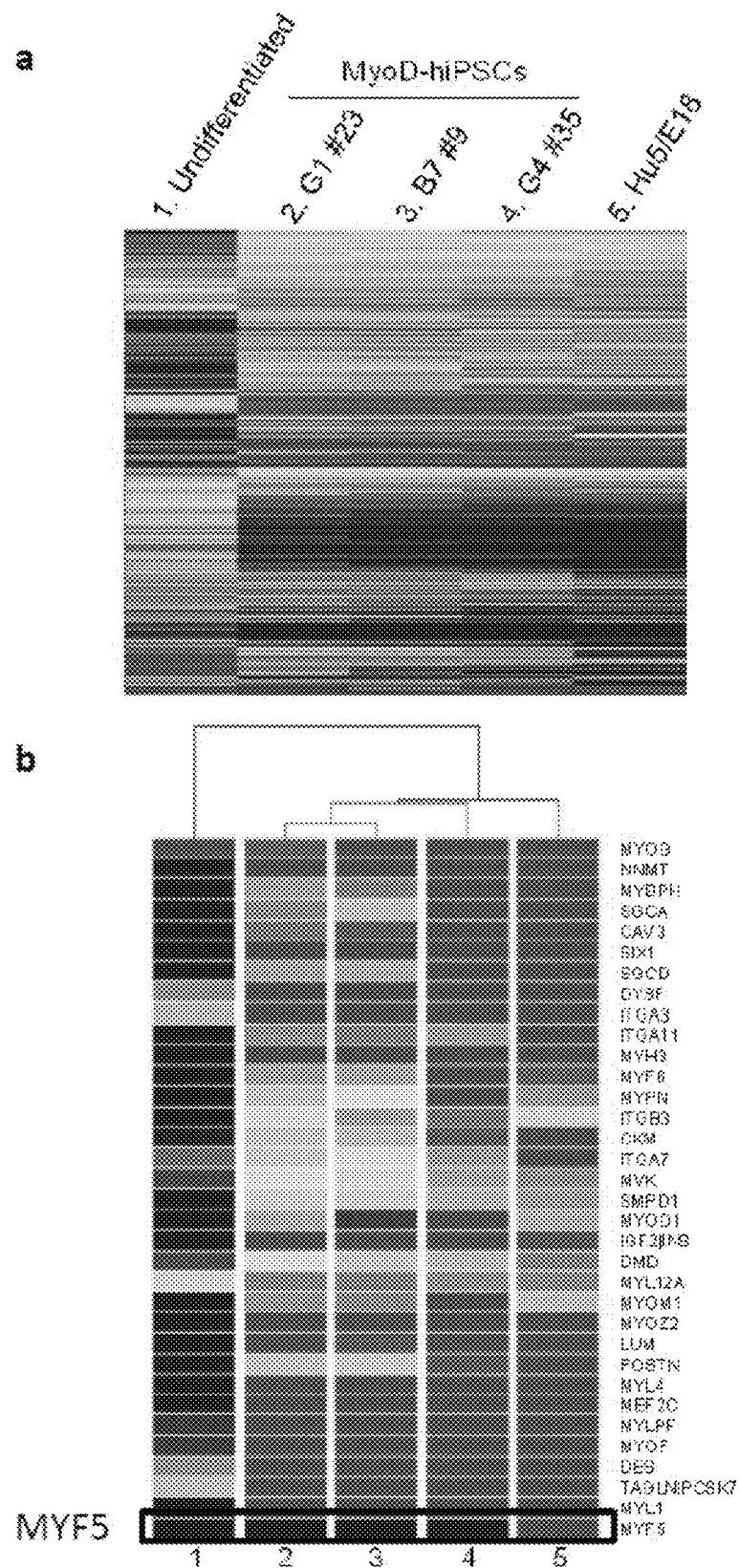
FIG. 10a shows the heat map of global mRNA expression comparing undifferentiated hiPSC and differentiated myogenic cells. Red shows up-regulated genes and blue shows down-regulated genes.
FIG. 10b shows the heat map of mRNA expression for selected markers associated with myofiber comparing undifferentiated hiPSC and differentiated myogenic cells. Red shows up-regulated genes and blue shows down-regulated genes. "1", "2", "3", "4" and "5" means undifferentiated cells, G1 #23 MyoD-hiPSCs, B7 #9 MyoD-hiPSCs, G4 #35 MyoD-hiPSCs and Hu5/E18, respectively.

To assess myogenic properties, histological analyses were performed. Although, undifferentiated hiPSCs had few mitochondria, differentiated MyoD-hiPSCs had many mitochondria surrounding nuclei (FIG. 9c). Besides, differentiated MyoD-hiPSCs expressed skeletal muscle actin and CK-M, which were mature myocytes markers (FIG. 9d). All these features suggest that Dox-induced myogenic cells derived from MyoD-hiPSCs have mature myocytes character. The global gene profiles of differentiated MyoD-hiPSCs were analyzed by mRNA Microarray, comparing with differentiated human myoblast cell line Hu5/E1826, and undifferentiated hiPSCs (FIG. 10). The global gene profiles of differentiated MyoD-hiPSCs were very similar to those of differentiated Hu5/E18 and quite different from those of undifferentiated hiPSCs (FIG. 10e). Furthermore, focusing on a muscle lineage, mRNA expression profiles of selected specific genes associated with muscle differentiation were analyzed. Differentiated MyoD-hiPSCs showed high expression of the selected genes as well as differentiated Hu5/E18, except for Myf5 which is a upstream transcription factor of MyoD1 (FIG. 10f). Taken together, Dox-induced myogenic cells generated from MyoD-hiPSCs represent mature myocytes similar to differentiated human myoblast cells. However, the process of differentiation is quite different, because the MyoD-hiPSCs do not express Myf5 unlike human myoblast and may jump into MyoD1 positive myogenic cells from undifferentiated cells.

Figure 11:
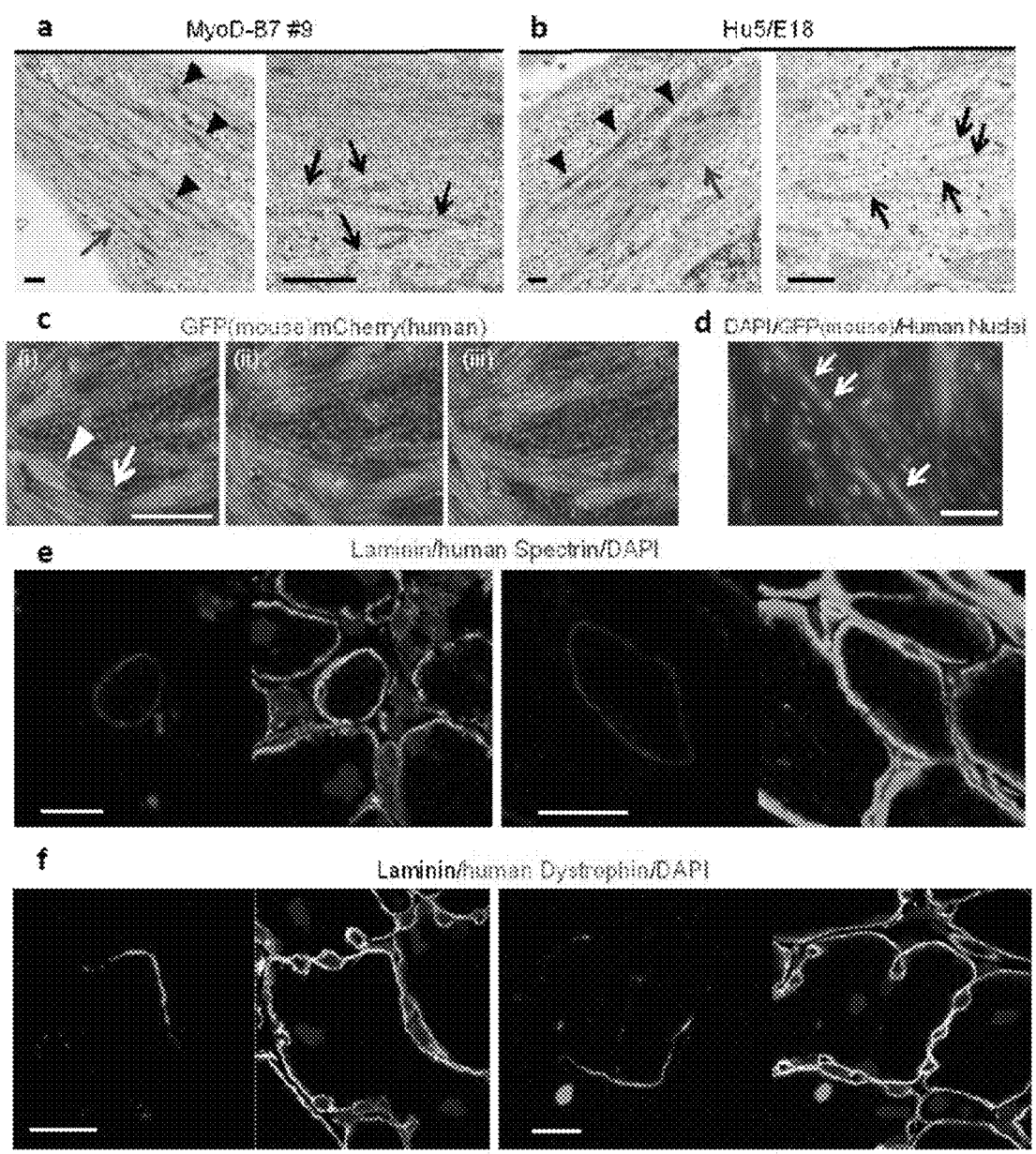
FIGS. 11a and 11b shows the Electron microscopy of differentiated MyoD-hiPSCs (a) and immortalized human myoblast Hu5/E18 cells (b). At each left panel, a red arrow shows a muscle fiber and arrowheads show future Z band. At each right panel, arrows show myosin fiber. Scale bars show 500 nm.
FIG. 11c shows serial photographs of differentiated MyoD-hiPSCs co-cultured with C2C12 cells. A human derived red cell (white arrow) fused with a mouse derived green cell (white arrowhead) and became a yellow cell (red arrow). A scale bar shows 100 µm.
FIG. 11d shows image for immunohistochemistry of MyoD-hiPSCs co-cultured with C2C12 cells. Arrows show human nuclei in a murine myofiber. Scale bars show 100 µm.
FIGS. 11e and 11f shows the image of immunohistochemistry of TA muscles from NOD-DMD mice after 28 days after transplantation of d6 MyoD-hiPSCs.

Next, functional properties of Dox-induced myogenic cells were assessed. Structural analysis by electron microscopy revealed that the differentiated MyoD-hiPSCs have myofibrils (FIG. 11a, red arrow) containing future Z line-like structures (FIG. 11a, arrowheads), and myosin fibers (FIG. 11a, arrows) similar to differentiated Hu5/E18 (FIG. 11b). To assess whether such structural properties are enough to contract, electric stimulation was loaded into Dox-induced myogenic cells. Actually, induced myofiber could contract coincident with electric pulse. It is a discriminative character that myogenic cells can fuse each other and form multi-nuclei myofibers. To address the fusion potential, differentiated MyoD-hiPSCs were co-cultured with mouse myoblast cell line C2C1229. Two days after co-culture, mCherry positive human myogenic cells fused with GFP positive murine myogenic cells (FIG. 11c). Several human nuclei were detected in a murine myofiber, demonstrating cell fusion in vitro (FIG. 11d, arrow).

Finally, we transplanted differentiated MyoD-hiPSCs to tibialis anterior muscle (TA muscle) of non-obese diabetic/severe-combined immunodeficient-duchenne muscular dystrophy null30 (NOD/scid-DMD) mice (Online Method). On 28 days after transplantation, although the signals were a few, specific staining of anti-human spectrin (FIG. 11e) and anti-human dystrophin (FIG. 11f) was detected in mouse TA muscle. These results indicate that MyoD-hiPSC-derived myocytes have fusion potential in vitro and in vivo. Taken together, Dox-induced myogenic cells derived from MyoD-hiPSCs achieve some functional properties as muscle similar to differentiated human myoblast cells.

Analysis for Differentiated Cells Derived from Miyoshi Myopathy (MM) hiPSCs

Figure 12:
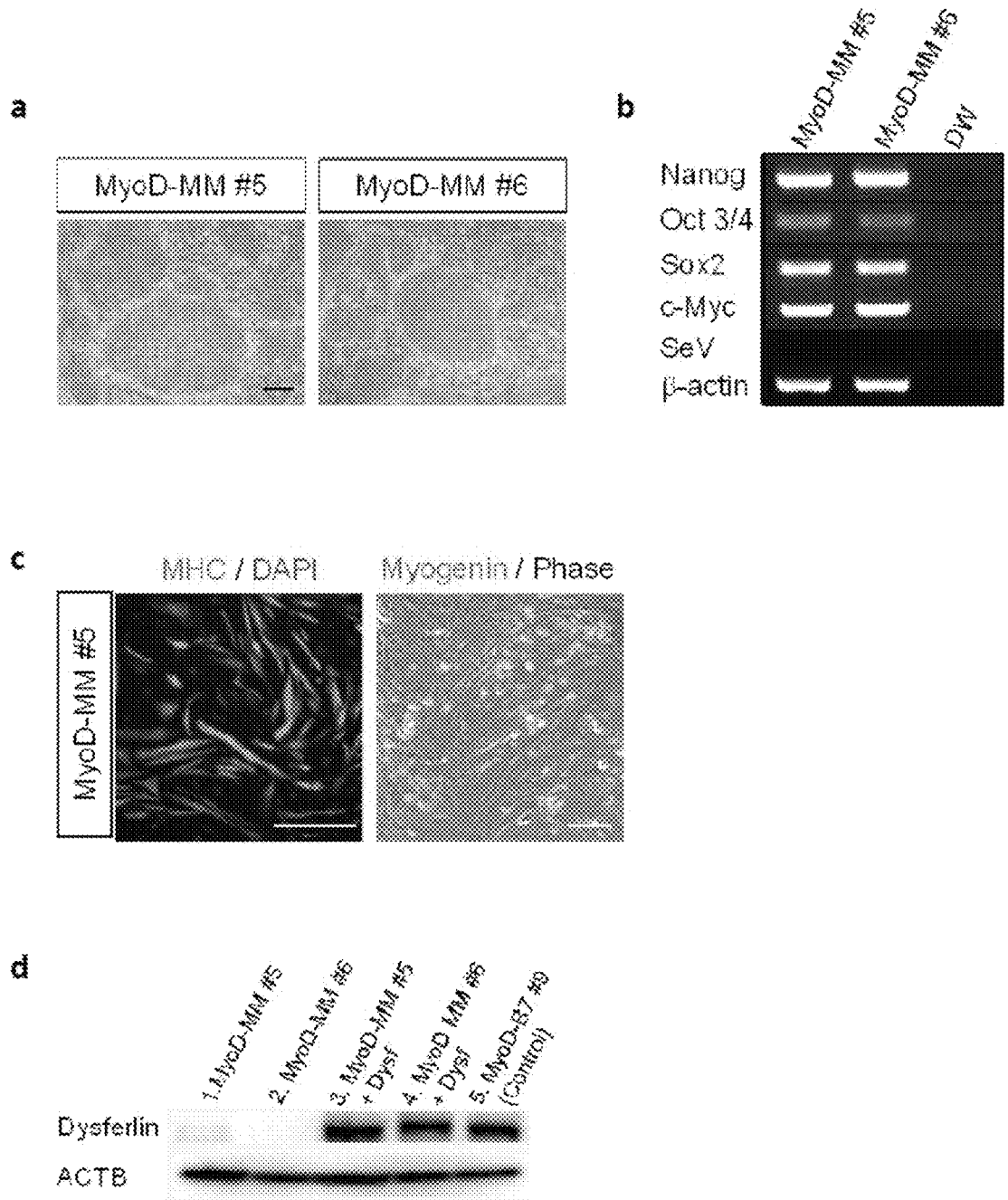
FIG. 12a shows the image of Miyoshi myopathy (MM) patient-derived hiPSC clones (MyoD-MM #5 and MyoD-MM #6) transfected Tet-MyoD1 vector. A scale bar shows 200 µm.
FIG. 12b shows the result of assessment of endogenous pluripotent stem cell markers in MyoD-MM hiPSCs.
FIG. 12c shows the image of differentiated MyoD-MM hiPSCs according to defined protocol. MHC positive (left), or Myogenin positive (right) cells were observed dominantly. Scale bars show 100 µm.
FIG. 12d shows the result of Western blotting for confirmation of dysferlin expression of the myofibers from each MyoD-MM hiPSCs (lane 1, 2), rescued MyoD-MM hiPSCs which expressed full-length Dysferlin cDNA driven by EF1α promoter (lane 3, 4), and control non-diseased MyoD-hiPSCs (lane 5).

Two MM patient-derived hiPSC clones introduced Tet-MyoD1 vector (MyoD-MM #5 and MyoD-MM #6) were morphologically identical to the other hiPSCs (FIG. 12a), and expressed endogenous undifferentiated marker genes without residual expression of SeV vectors (FIG. 12b). MyoD-MM hiPSCs could differentiate into MHC or Myogenin positive mature myocytes (FIG. 12c).

Next, two rescue clones (as indicated by +Dysf) were established from MyoD-MM hiPSCs by over-expression of Dysferlin. Dysferlin expression was confirmed in the two rescue clones as well as control MyoD-B7 #9, while MyoD-MM #5 and #6 did not express Dysferlin (FIG. 12d).

Figure 13:
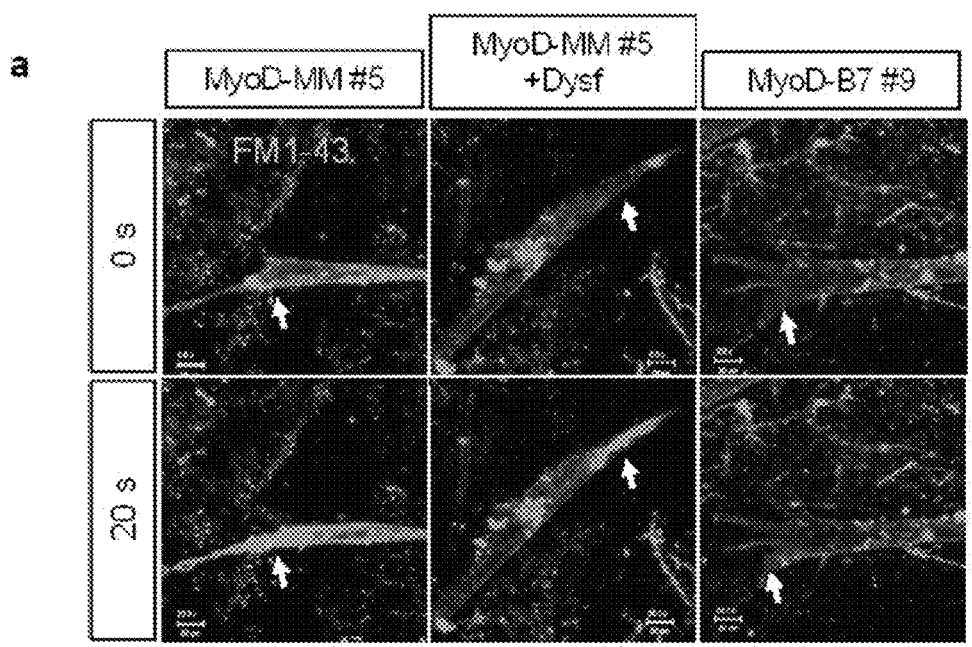
FIG. 13a shows the image of entry of FM1-43 fluorescent dye (green) into differentiated myofibers from MyoD-MM #5 (left), rescued MyoD-MM #5 with Dsyferlin expression (middle), or control MyoD-hiPSC clone B7 #9 (right), before (0 sec) and second after (20 sec) two photon laser-induced damage of the sarcolemmal membrane (arrow). Scale bars show 20 µm.
FIG. 13b shows time course data of accumulation of FM1-43 dye in laser-damaged myofibers derived from B7 #9 (black circles), MyoD-MM hiPSCs (red or blue triangles) and rescued MyoD-hiPSCs with Dysferlin expression (red or blue circles) (n=5 in each clones). The data are listed as mean±S.E. (error bars).
Figure 13:
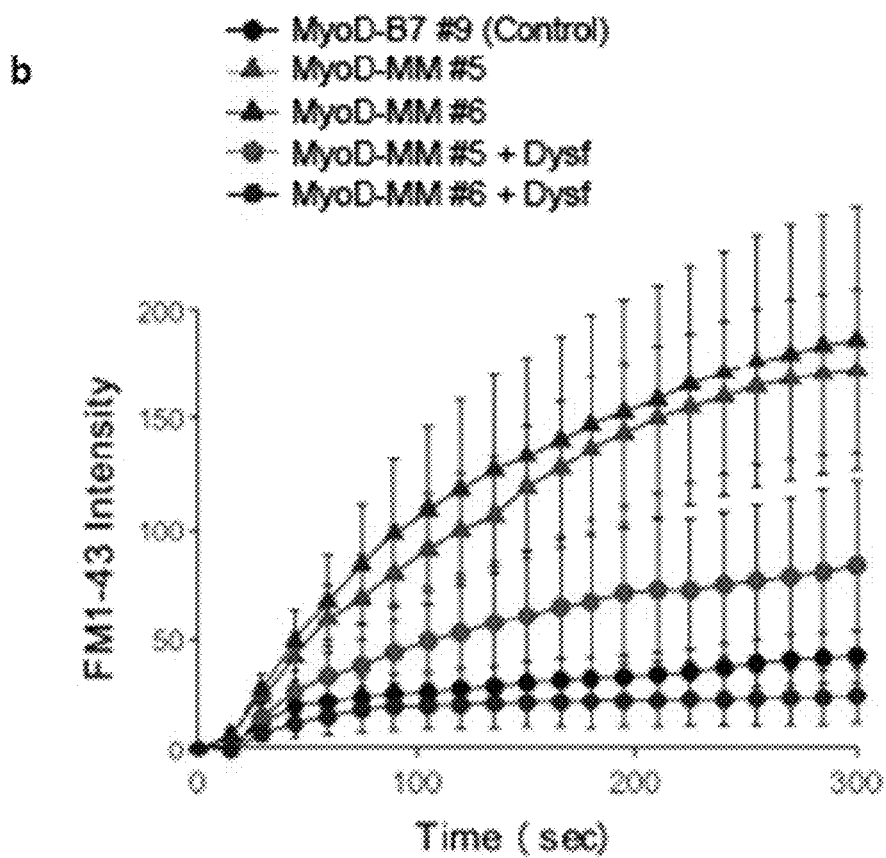

Finally, the membrane repair function to recreate pathological conditions was assessed in both intact- and rescued-MM patient derived iPSCs with a control MyoD-hiPSC (FIGS. 12e and 12f). A myofiber from the MyoD-MM #5 displays over uptake of FM1-43 in all cytoplasmic lesion indicating defective membrane repair following two-photon laser-induced injury of the sarcolemma (FIG. 13a left), while myofibers from MyoD-MM #5 +Dysf and MyoD-B7 #9 display focal uptake of FM1-43 at damaged area (FIG. 13a middle and right). Indeed, the apparently unimpeded uptake of FM 1-43 observed in MM patient-derived myofibres, over-expression of Dysferlin promoted efficient membrane resealing similar to control level (FIG. 13b). Thus, pathological conditions of MM with patient-derived iPSCs were successfully recreated. It is suggested that this system is useful to establish a drug screening system for MM, because of its reproducibility, high efficiency and short induction periods.

Production of Tet-Myf5 hiPSC and Selection of Clone

The aforementioned Tet-Myf5 vector was transfected into human iPS cell, and a single colony was picked up from the cell group that obtained neomycin resistance to give 24 clones. The clones were divided into a Dox-addition group and a non-addition group, and clones were selected by analysis of mCherry expression 48 hr later (FIGS. 14a and 14b). Among the 24 clones, Clone Nos. 2, 18 and 21 (#2, #18, #21) were selected, which showed comparatively high expression of mCherry (FIG. 14c). mRNA was recovered 48 hr later in each of the Dox addition group and non-addition group, and the gene expression was analyzed by PCR (FIG. 14d). The Dox non-addition group showed no expression with leakage of exogenous Myf5 (Tg), or any expression of not only endogenous Myf5 (Endo) but also MyoD and Myogenin induced by Myf5 (FIG. 14d). The Dox-addition group showed expressions of both MyoD (Tg) and MyoD (Endo) in all clones, which confirms that Dox induces exogenous gene expression and also expresses endogenous skeletal muscle differentiation gene (FIG. 14d).

Skeletal Muscle Cell Induction from Tet-Myf5 hiPSC Clone

Figure 15:
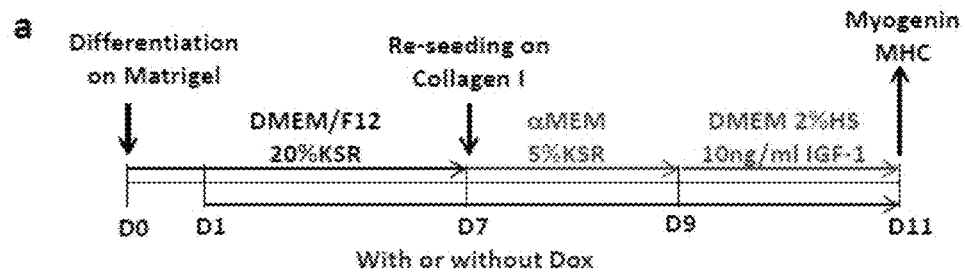
FIG. 15a shows the protocol of skeletal muscle cell induction of respective iPS cell lines (#2, #18 and #21) introduced with a tetracycline responsive Myf5 expression piggyBac vector.
FIG. 15b shows fluorescence microscope images of the expression of mCherry and phase contrast microscope images showing the changes of cell form at 48 hr after Dox addition (Dox(+) 48 h) or non-addition (Dox (−)) in Myf5 induction expression cell line.
FIG. 15c shows stained images with an anti-Myogenin antibody and an anti-MHC antibody, after skeletal muscle cell induction in clone #2.
Figure 15:
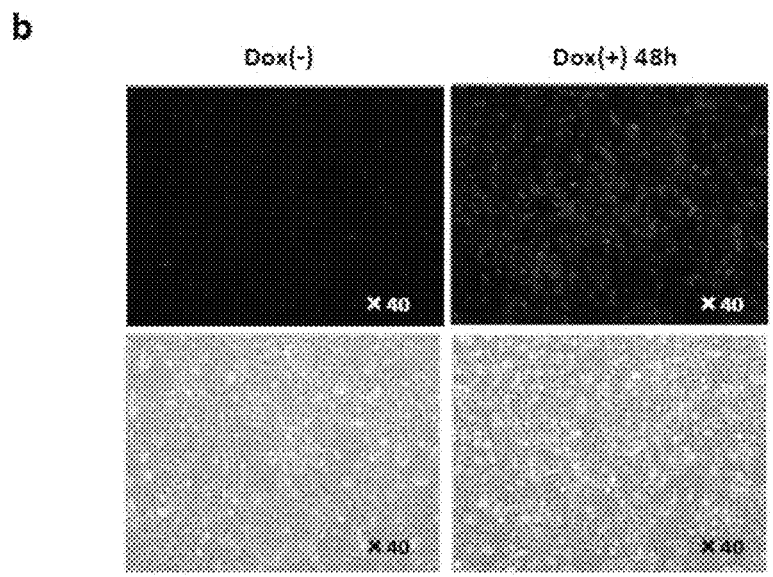
Figure 15:
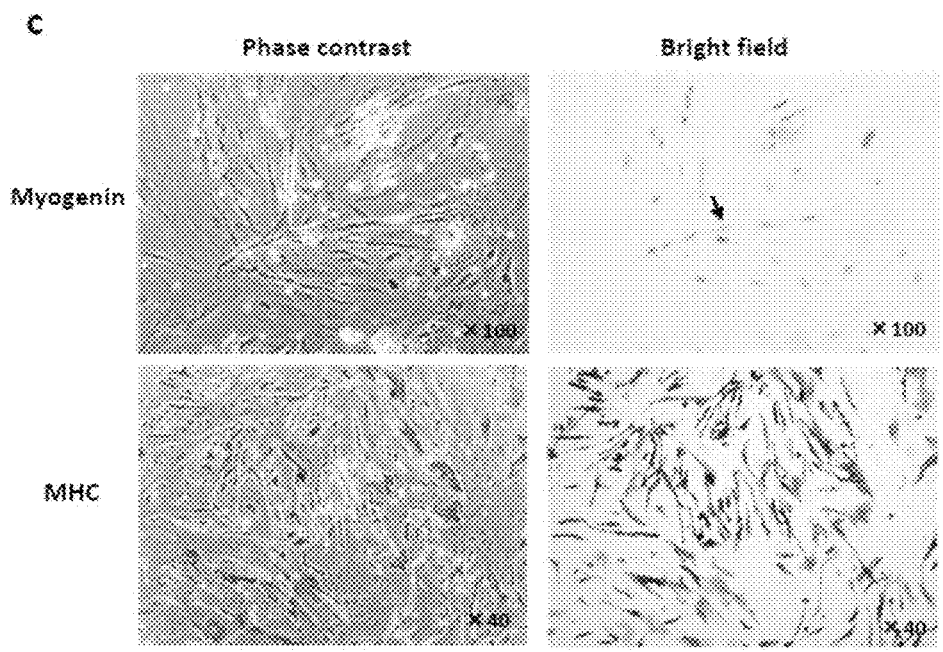

As shown in FIG. 15a, differentiation of Tet-Myf5 hiPSC was induced. The Dox-addition group showed highly uniform expression of mCherry 48 hr later (FIG. 15b, upper panel) and simultaneously showed change into a spindle-shaped cell form as compared to the Dox non-addition group (FIG. 15b, lower panel). On Day 11 from the differentiation, expression of Myogenin and MHC was observed. The 3 clones of #2, #18 and #21 showed differentiation into Myogenin positive and MHC positive skeletal muscle cell. The expressions of Myogenin and MHC in #2 are shown in FIG. 15c. The upper panel shows the expression of Myogenin, where polynuclear Myogenin positive cells are to observed on one muscle fiber (FIG. 15c, arrow). The lower panel shows the expression of MHC, where uniform differentiation of very many skeletal muscle cells is observed. From the above results, it has been found that iPS cell can be differentiated into a skeletal muscle cell efficiently even by forced expression of Myf5 with a tetracycline-responsive vector.

This application is based on U.S. provisional patent application No. 61/561,586, the contents of which are incorporated in full herein.

The invention claimed is:

1. A method of producing a skeletal muscle cell from a pluripotent stem cell, comprising:
   (i) providing a pluripotent stem cell that does not express exogenous MyoD and Myf5;
   (ii) culturing the pluripotent stem cell on a matrix-coated culture dish and in a bFGF-free basal medium, such that the pluripotent stem cell does not maintain pluripotency but does not specifically differentiate into a skeletal muscle cell;
   (iii) expressing one or more exogenous factors selected from MyoD, Myf5 and nucleic acids encoding them in the cell obtained in step (ii); wherein the expressing begins no later than 3 days after the start of step (ii) and continues for at least 7 days after the start of step (ii), and wherein the cell is cultured on a matrix-coated dish in a myogenic medium, and
   (iv) further culturing the cell obtained in step (iii) in a myogenic medium on a matrix-coated dish for a sufficient amount of time to induce differentiation of the cell obtained in step (iii) into a skeletal muscle cell, wherein the differentiation of the cell obtained in step (iii) into the skeleton muscle cell occurs with greater efficiency than when the pluripotent stem cell of step (i) is directly subjected to steps (iii) and (iv).

2. The method according to claim 1, wherein the pluripotent stem cell is human pluripotent stem cell.

3. The method according to claim 1, wherein the culture period of step (ii) is up to 1 day.

4. The method according to claim 1, wherein the bFGF-free basal medium is supplemented with a serum or a serum substitute.

5. The method according to claim 1, wherein the culturing of step (iv) is performed in a culture medium containing horse serum.

6. The method according to claim 1, wherein the expression of the one or more exogenous factors is maintained for not less than 5 days and not more than 10 days.

7. The method according to claim 1, wherein the pluripotent stem cell contains a nucleic acid encoding MyoD or Myf5 under the control of an element that promotes transcription of the nucleic acid responsive to a drug, and wherein step (iii) is performed by culturing the cell obtained in step (ii) in the presence of the drug.

8. A method of screening for an agent for the treatment or prophylaxis of myopathy, comprising
   (i) generating skeletal muscle cells using the method of claim 1 to provide a line of skeletal muscle cells with myopathy in an amount sufficient for performing the screening, wherein the pluripotent stem cell used in the method of claim 1 is from a patient with myopathy;
   (ii) contacting the skeletal muscle cells with test substances;
   (iii) evaluating change in a pathological condition of the skeletal muscle cells; and
   (iv) selecting a test substance that has mitigated the pathological condition as a candidate of a therapeutic or prophylactic agent for myopathy.

9. The method according to claim 6, wherein the expression of the one or more exogenous factors is maintained for 6 days.

10. The method according to claim 8, wherein the myopathy is selected from the group consisting of muscular dystrophy, distal myopathy and Miyoshi myopathy.

11. The method according to claim 1, wherein the differentiation efficiency is retained at 70% or more with low levels of clonal variation.

12. A method of screening for an agent for the treatment or prophylaxis of myopathy, comprising
   (i) generating skeletal muscle cells using the method of claim 11 to provide a line of skeletal muscle cells with myopathy in an amount sufficient for performing the screening, wherein the pluripotent stem cell used in the method of claim 1 is from a patient with myopathy;
   (ii) contacting the skeletal muscle cells with test substances;
   (iii) evaluating change in a pathological condition of the skeletal muscle cells; and
   (iv) selecting a test substance that has mitigated the pathological condition as a candidate of a therapeutic or prophylactic agent for myopathy,
   wherein steps (i) to (iv) are performed for a plurality of skeletal muscle cell lines derived from one iPS clone by a plurality of differentiation operations.

13. The method of claim 1, wherein the matrix-coated dish is a dish coated with collagen, extracellular matrix, gelatin, or a combination thereof.

14. The method of claim 13, wherein the matrix-coated dish is a dish coated with collagen I.

15. The method of claim 1, wherein the myogenic medium comprises serum or a serum replacement.

16. The method of claim 15, wherein the myogenic medium comprises horse serum.

17. The method of claim 1, wherein the myogenic medium comprises IGF-1.

* * * * *